(12) United States Patent
Kurata et al.

(10) Patent No.: US 10,592,812 B2
(45) Date of Patent: Mar. 17, 2020

(54) INFORMATION PROCESSING APPARATUS AND INFORMATION PROCESSING METHOD

(71) Applicant: SONY CORPORATION, Tokyo (JP)

(72) Inventors: Masatomo Kurata, Tokyo (JP); Masanori Katsu, Tokyo (JP); Sota Matsuzawa, Tokyo (JP)

(73) Assignee: SONY CORPORATION, Tokyo (JP)

( * ) Notice: Subject to any disclaimer, the term of this patent is extended or adjusted under 35 U.S.C. 154(b) by 873 days.

(21) Appl. No.: 15/110,440

(22) PCT Filed: Oct. 16, 2014

(86) PCT No.: PCT/JP2014/077597
§ 371 (c)(1),
(2) Date: Jul. 8, 2016

(87) PCT Pub. No.: WO2015/107737
PCT Pub. Date: Jul. 23, 2015

(65) Prior Publication Data
US 2016/0335557 A1 Nov. 17, 2016

(30) Foreign Application Priority Data
Jan. 20, 2014 (JP) ................................ 2014-007920

(51) Int. Cl.
*G06F 15/18* (2006.01)
*G06N 7/00* (2006.01)
(Continued)

(52) U.S. Cl.
CPC ............... *G06N 7/005* (2013.01); *A61B 5/04* (2013.01); *A61B 5/1038* (2013.01); *A61B 5/11* (2013.01);
(Continued)

(58) Field of Classification Search
CPC ...................................................... G06F 1/163
(Continued)

(56) References Cited

U.S. PATENT DOCUMENTS 8,783,264 B2 * 7/2014 Levendowski .......... A61B 5/11
128/871
2003/0120183 A1 * 6/2003 Simmons .................. A61F 4/00
600/595
(Continued)

FOREIGN PATENT DOCUMENTS

JP 2004-184351 A 7/2004
JP 2006-192276 A 7/2006
(Continued)

OTHER PUBLICATIONS

Extended European Search Report of EP Patent Application No. 14878498.6, dated Jun. 19, 2017, 07 pages.
(Continued)

*Primary Examiner* — David R Vincent
(74) *Attorney, Agent, or Firm* — Chip Law Group

(57) ABSTRACT

Provided is an information processing apparatus including: a behavior recognition mode setting unit that sets a behavior recognition mode on a basis of wearing position information of a setting target device, a behavior recognition unit that recognizes a user's behavior on a basis of the set behavior recognition mode and a detection value of a sensor corresponding to the setting target device, and a process control unit that controls execution of a process corresponding to the recognized user's behavior.

15 Claims, 19 Drawing Sheets

(51) Int. Cl.

| | |
|---|---|
| *G06F 1/16* | (2006.01) |
| *G06F 3/0346* | (2013.01) |
| *G06F 3/038* | (2013.01) |
| *A61B 5/00* | (2006.01) |
| *A61B 5/04* | (2006.01) |
| *A61B 5/11* | (2006.01) |
| *A61B 5/113* | (2006.01) |
| *A61B 5/103* | (2006.01) |
| *G06K 9/00* | (2006.01) |
| *G06N 5/02* | (2006.01) |

(52) U.S. Cl.
CPC ............ *A61B 5/113* (2013.01); *A61B 5/1123* (2013.01); *A61B 5/681* (2013.01); *A61B 5/6803* (2013.01); *A61B 5/6814* (2013.01); *A61B 5/6822* (2013.01); *A61B 5/6823* (2013.01); *A61B 5/6824* (2013.01); *A61B 5/6825* (2013.01); *A61B 5/6829* (2013.01); *A61B 5/7264* (2013.01); *G06F 1/163* (2013.01); *G06F 1/1626* (2013.01); *G06F 1/1694* (2013.01); *G06F 3/038* (2013.01); *G06F 3/0346* (2013.01); *G06K 9/00342* (2013.01); *G06N 5/02* (2013.01); *A61B 5/0002* (2013.01); *A61B 5/1118* (2013.01); *A61B 5/742* (2013.01); *A61B 5/7405* (2013.01); *A61B 5/7455* (2013.01); *A61B 5/7465* (2013.01); *A61B 2562/0219* (2013.01); *A61B 2562/06* (2013.01)

(58) Field of Classification Search
USPC ...................................... 706/15, 45
See application file for complete search history.

(56) References Cited

U.S. PATENT DOCUMENTS

| | | |
|---|---|---|
| 2006/0161079 A1 | 7/2006 | Choi et al. |
| 2009/0326406 A1 | 12/2009 | Tan et al. |
| 2014/0343372 A1* | 11/2014 | Ahmed ............. A61B 5/02405 600/301 |
| 2016/0107309 A1* | 4/2016 | Walsh .................. B25J 9/0006 248/550 |

FOREIGN PATENT DOCUMENTS

| | | |
|---|---|---|
| JP | 2006-340903 A | 12/2006 |
| JP | 2010-134802 A | 6/2010 |
| JP | 2012-522561 A | 9/2012 |
| WO | 2010/025467 A1 | 3/2010 |

OTHER PUBLICATIONS

Office Action for JP Patent Application No. 2015-557708, dated Sep. 11, 2018, 09 pages of Office Action and 03 pages of English Translation.

Office Action for EP Patent Application No. 14878498.6, dated Oct. 24, 2018, 07 pages of Office Action.

* cited by examiner

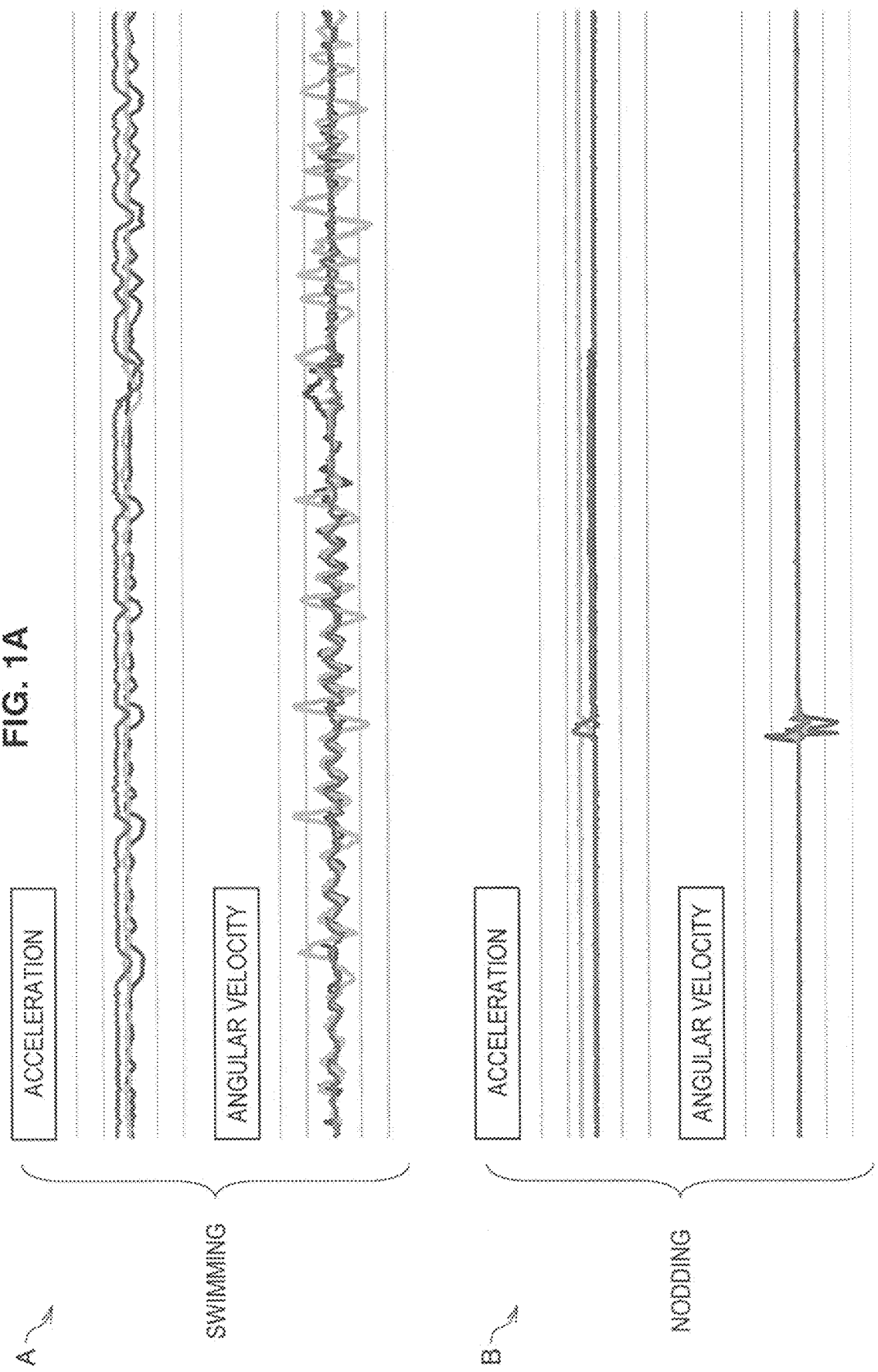

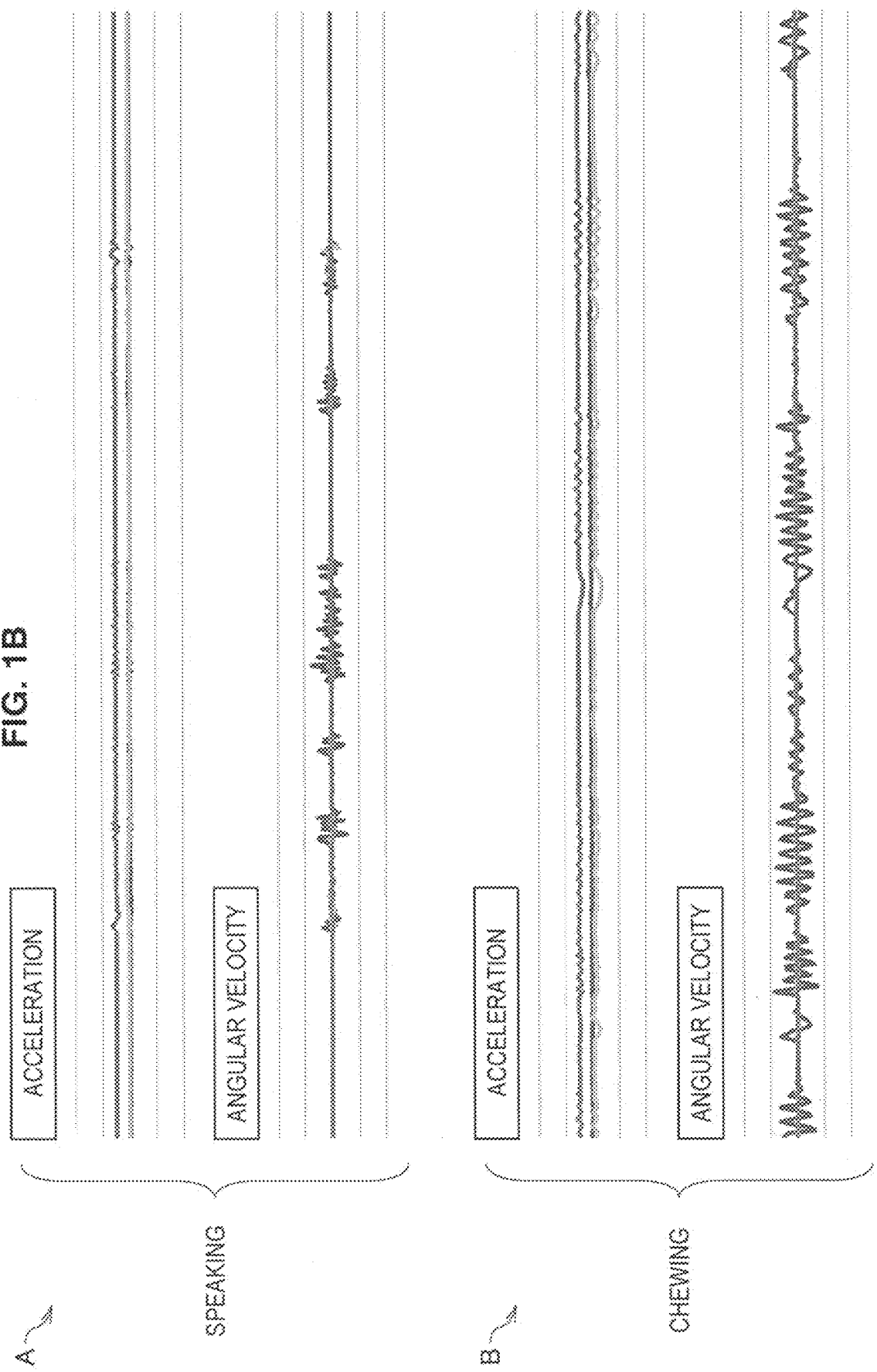

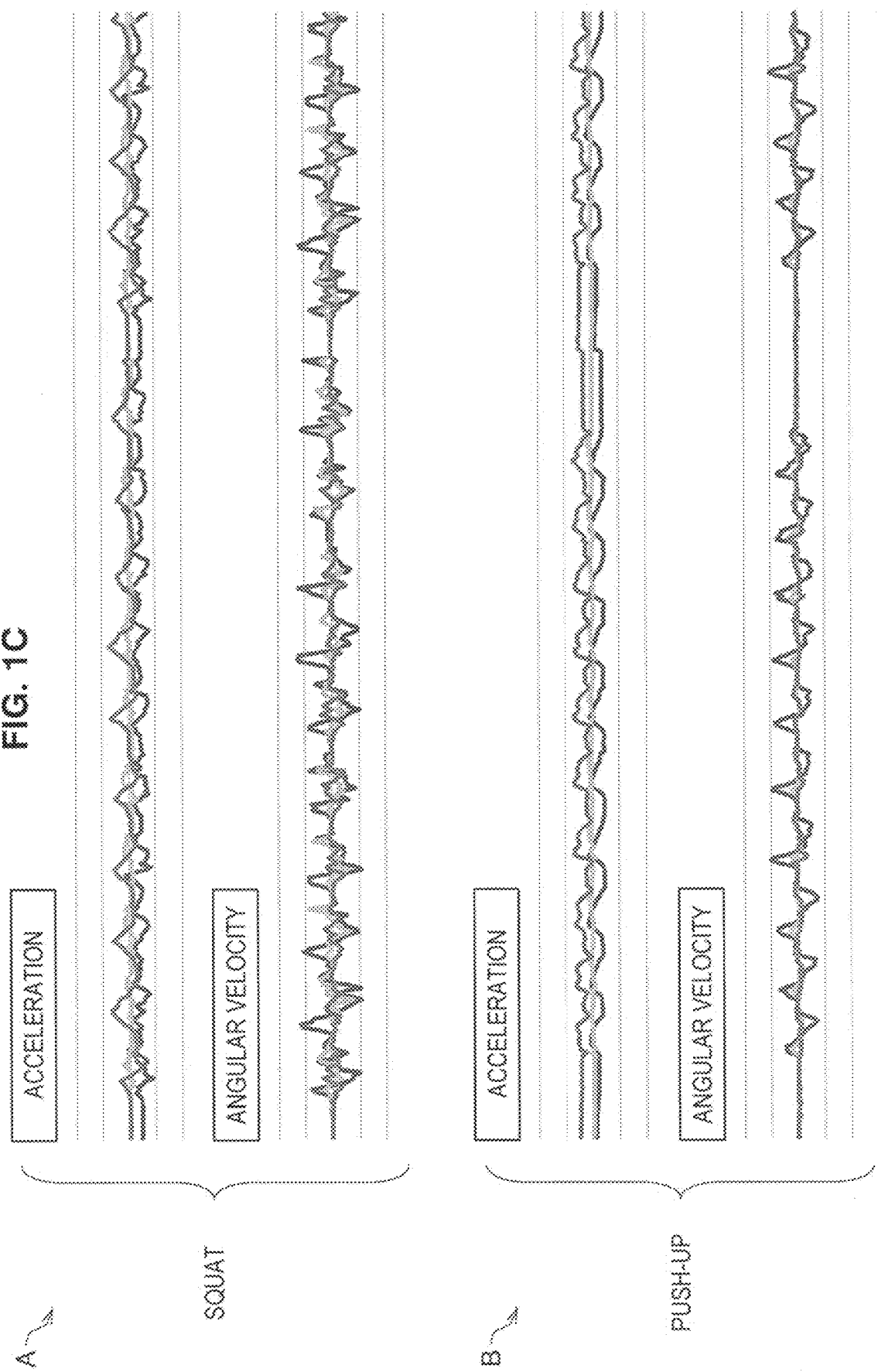

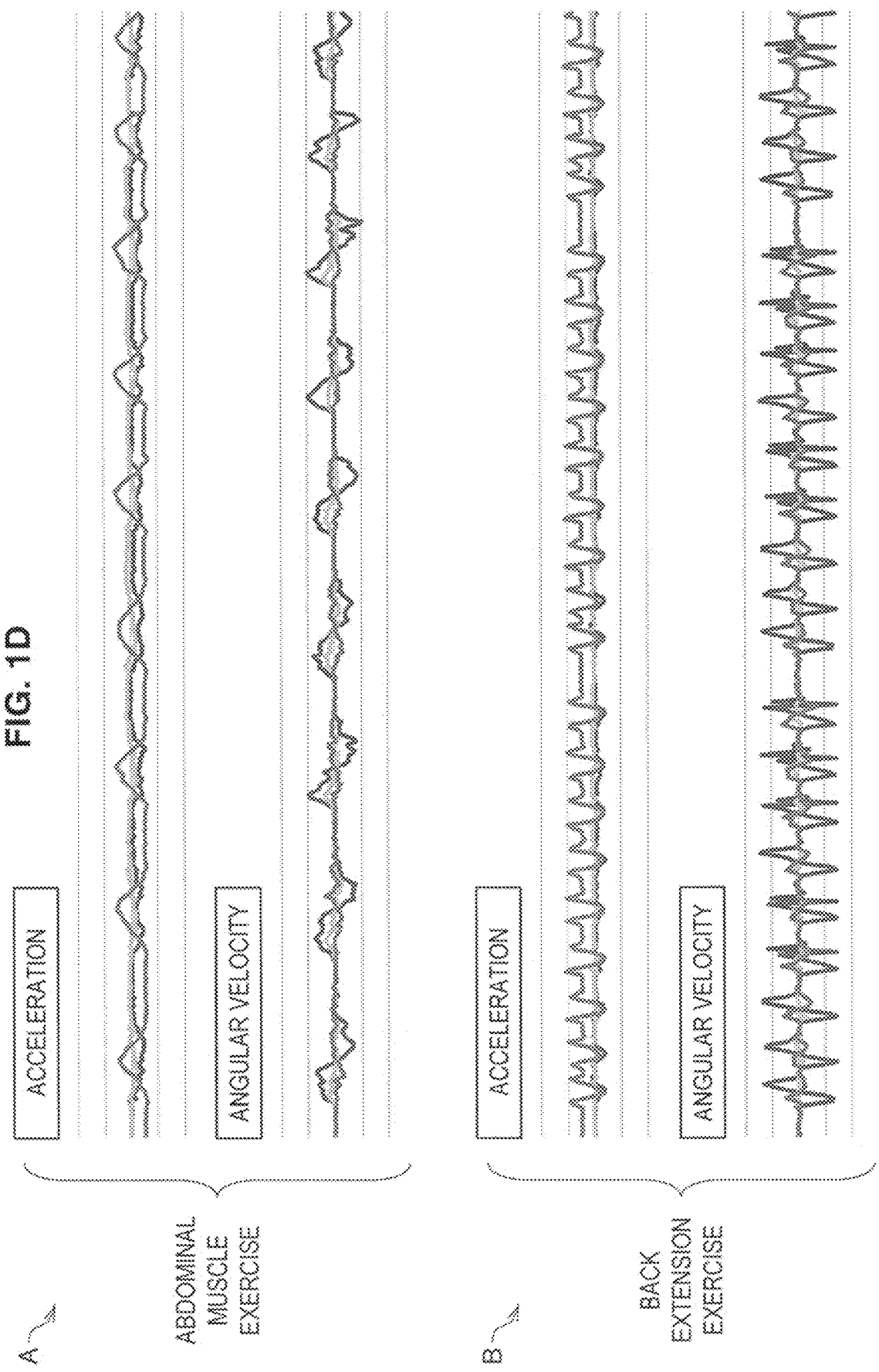

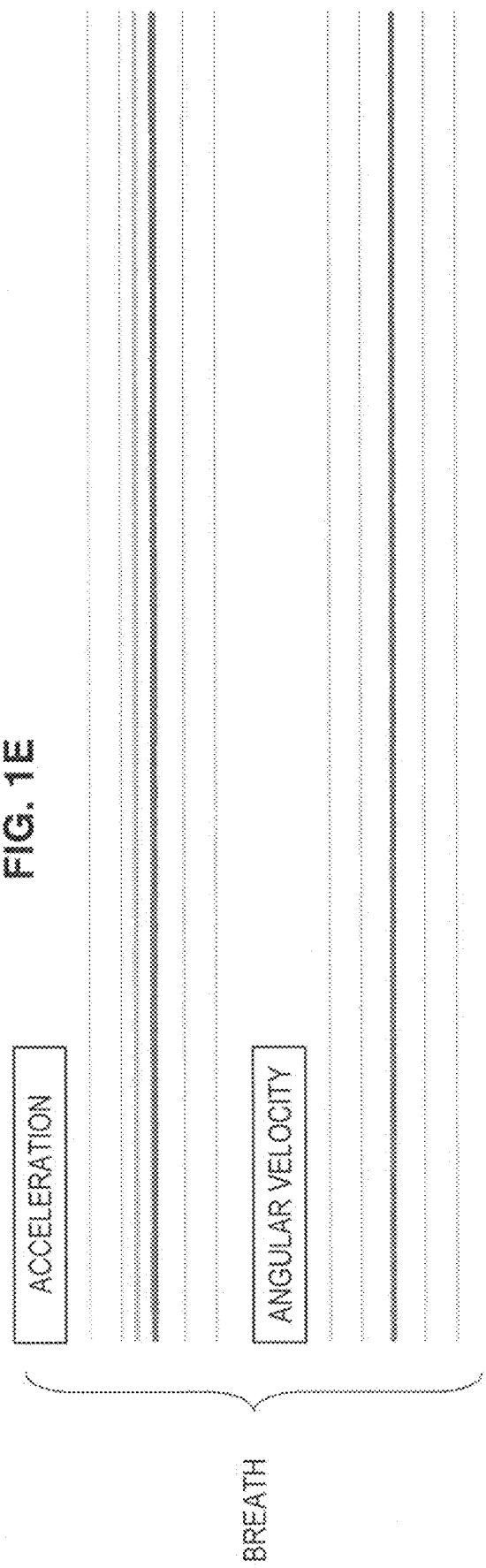

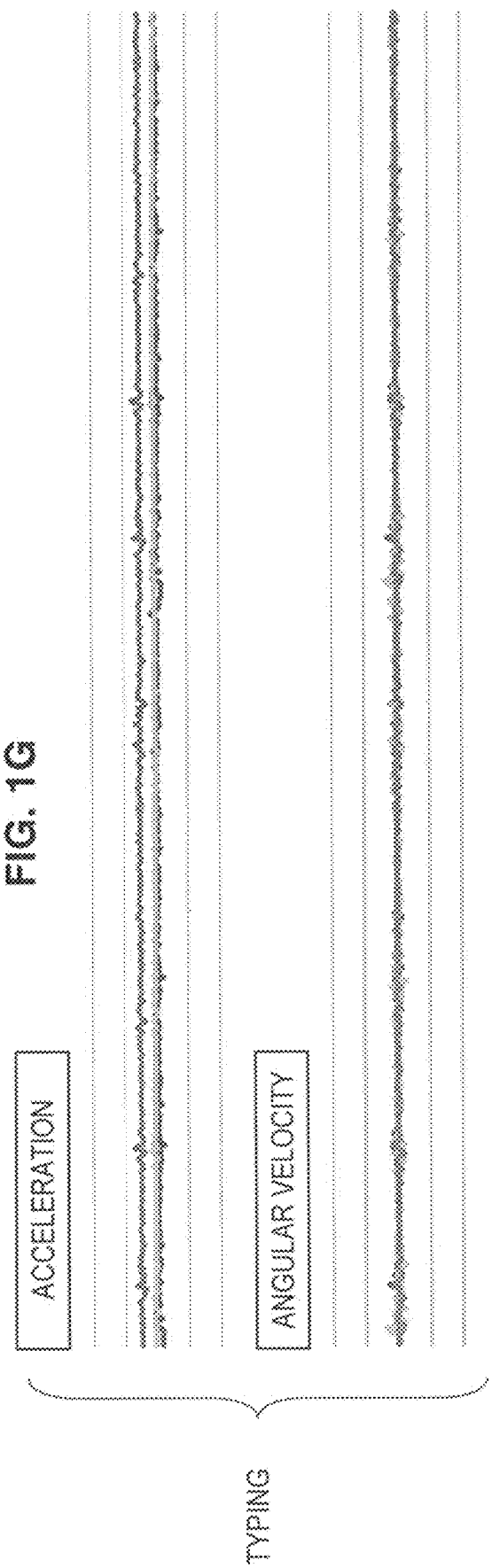

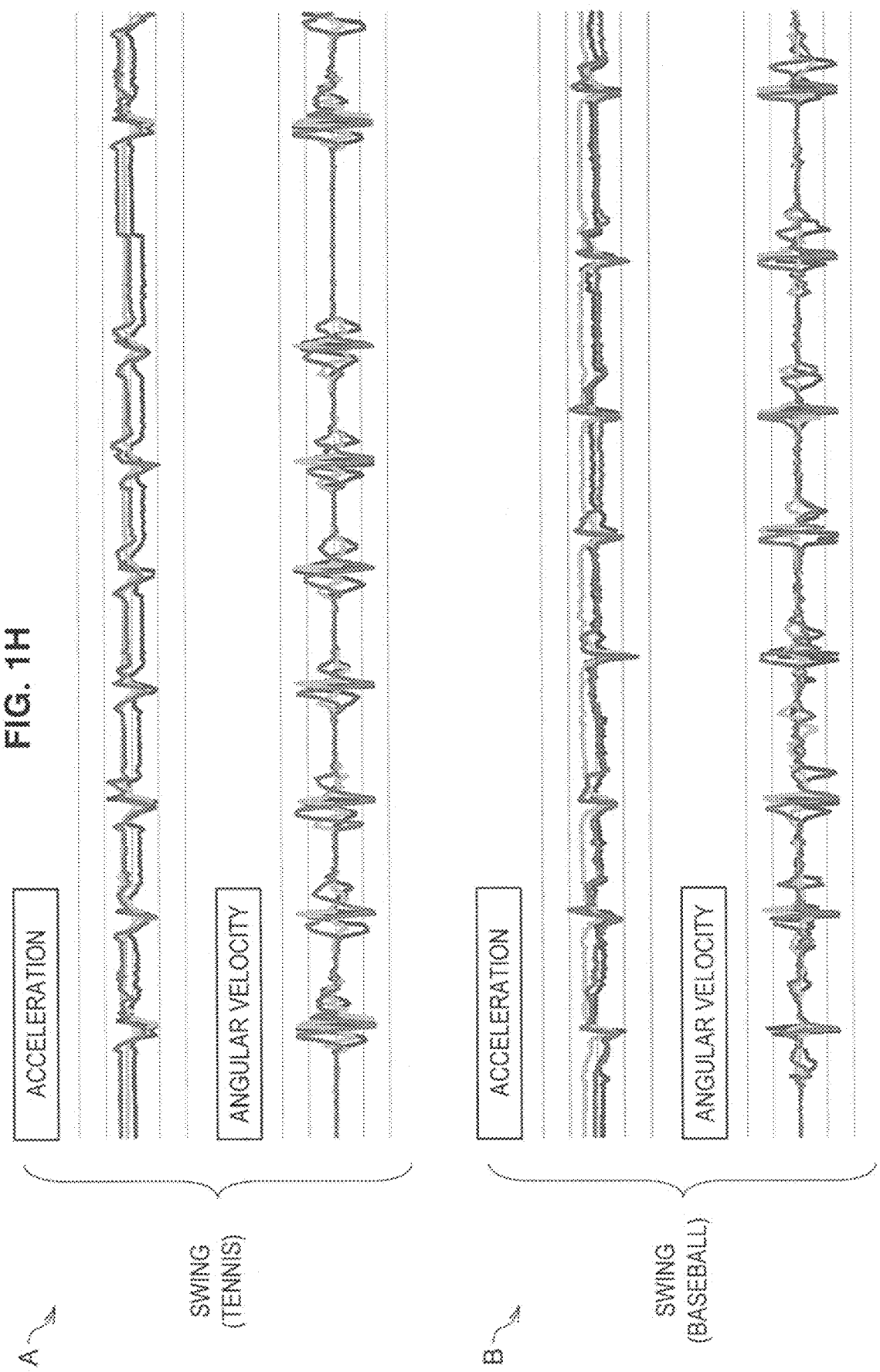

| REFERENCE WEARING POSITION | -100.0~-50.0 [cm] | -20.0~+50.0 [cm] | +40.0~+80.0 [cm] | +50.0~+100.0 [cm] |
|---|---|---|---|---|
| WAIST | ANKLE | WRIST | NECK | HEAD |

FIG. 10
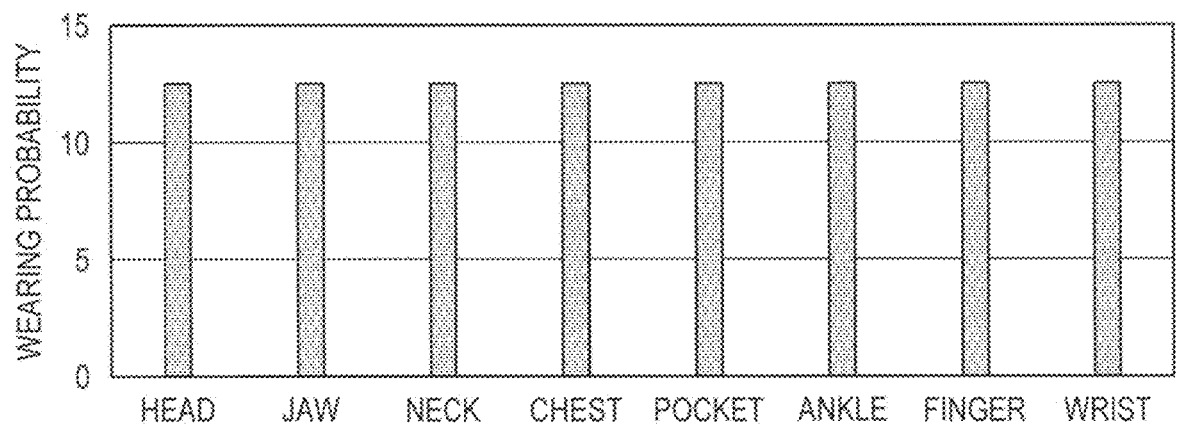
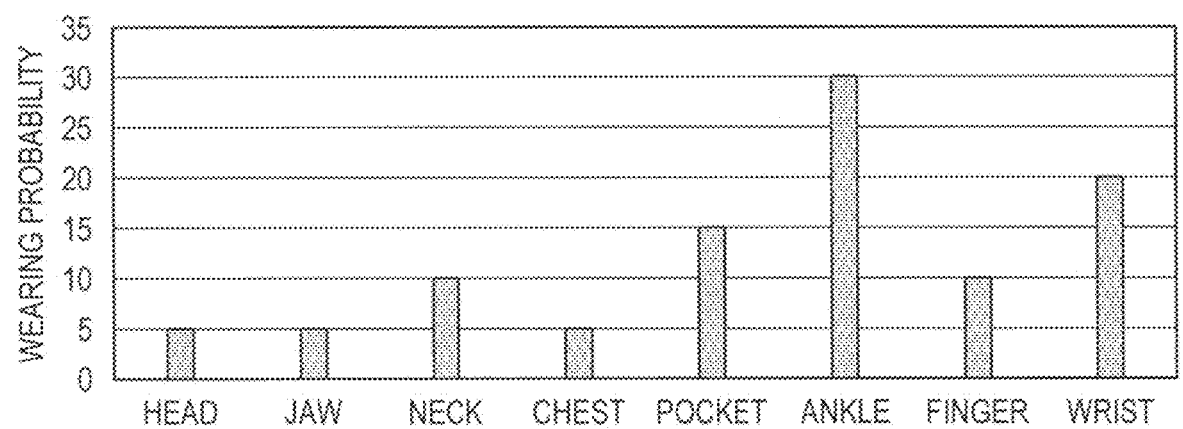

INFORMATION PROCESSING APPARATUS AND INFORMATION PROCESSING METHOD

TECHNICAL FIELD

The present disclosure relates to information processing apparatuses, information processing methods, and programs.

BACKGROUND ART

Technologies for recognizing behavior of a user and displaying a result of the recognition on a display screen have been developed. Examples of the technologies for recognizing behavior of a user and displaying a result of the recognition on a display screen include a technology described in the following Patent Literature 1.

CITATION LIST

Patent Literature

Patent Literature 1: JP 2010-134802A

SUMMARY OF INVENTION

Technical Problem

In recent years, the number of users who use wearable-type devices (hereinafter, referred to as "wearable device") that the users can use while wearing it, such as not only portable apparatuses like smartphones but also wristwatch-type devices, has been increasing. In addition, such as Lifelog, applications relating to behavior of a user also have been put to practical use, the applications using detection values from sensors loaded into the above-described apparatuses or external sensors attached to the above-described apparatuses.

However, when the recognition for user's behavior is performed simply using a detection value of a sensor, the accuracy of recognition for user's behavior is deteriorated or it may be failed to recognize user's behavior depending on the position at which a sensor-equipped device (or a device to which an external sensor is attached) is worn by the user.

The present disclosure provides a novel and improved information processing apparatus, information processing method, and program, capable of recognizing the user's behavior with higher accuracy and controlling a process corresponding to the recognized user's behavior.

Solution to Problem

According to the present disclosure, there is provided an information processing apparatus including: a behavior recognition mode setting unit configured to set a behavior recognition mode on a basis of wearing position information of a setting target device; a behavior recognition unit configured to recognize user's behavior on a basis of the set behavior recognition mode and a detection value of a sensor corresponding to the setting target device; and a process control unit configured to control execution of a process corresponding to the recognized user's behavior.

According to the present disclosure, there is provided an information processing method executed by an information processing apparatus, the information processing method including: a step of setting a behavior recognition mode on a basis of wearing position information of a setting target device; a step of recognizing user's behavior on a basis of the set behavior recognition mode and a detection value of a sensor corresponding to the setting target device; and a step of controlling execution of a process corresponding to the recognized user's behavior.

According to the present disclosure, there is provided a program for causing a computer to execute: a step of setting a behavior recognition mode on a basis of wearing position information of a setting target device; a step of recognizing user's behavior on a basis of the set behavior recognition mode and a detection value of a sensor corresponding to the setting target device; and a step of controlling execution of a process corresponding to the recognized user's behavior.

Advantageous Effects of Invention

According to the present disclosure, it is possible to recognize the user's behavior with higher accuracy and to control a process depending on the recognized user's behavior.

Note that the effects described above are not necessarily limited, and along with or instead of the effects, any effect that is desired to be introduced in the present specification or other effects that can be expected from the present specification may be exhibited.

BRIEF DESCRIPTION OF DRAWINGS

FIG. 1A is a diagram illustrated to describe an information processing method according to the present embodiment.

FIG. 1B is a diagram illustrated to describe an information processing method according to the present embodiment.

FIG. 1C is a diagram illustrated to describe an information processing method according to the present embodiment.

FIG. 1D is a diagram illustrated to describe an information processing method according to the present embodiment.

FIG. 1E is a diagram illustrated to describe an information processing method according to the present embodiment.

FIG. 1G is a diagram illustrated to describe an information processing method according to the present embodiment.

FIG. 1H is a diagram illustrated to describe an information processing method according to the present embodiment.

FIG. 10 is a diagram illustrated to describe a third example of a wearing position recognition process according to the present embodiment.

DESCRIPTION OF EMBODIMENT(S)

Figure 1F:
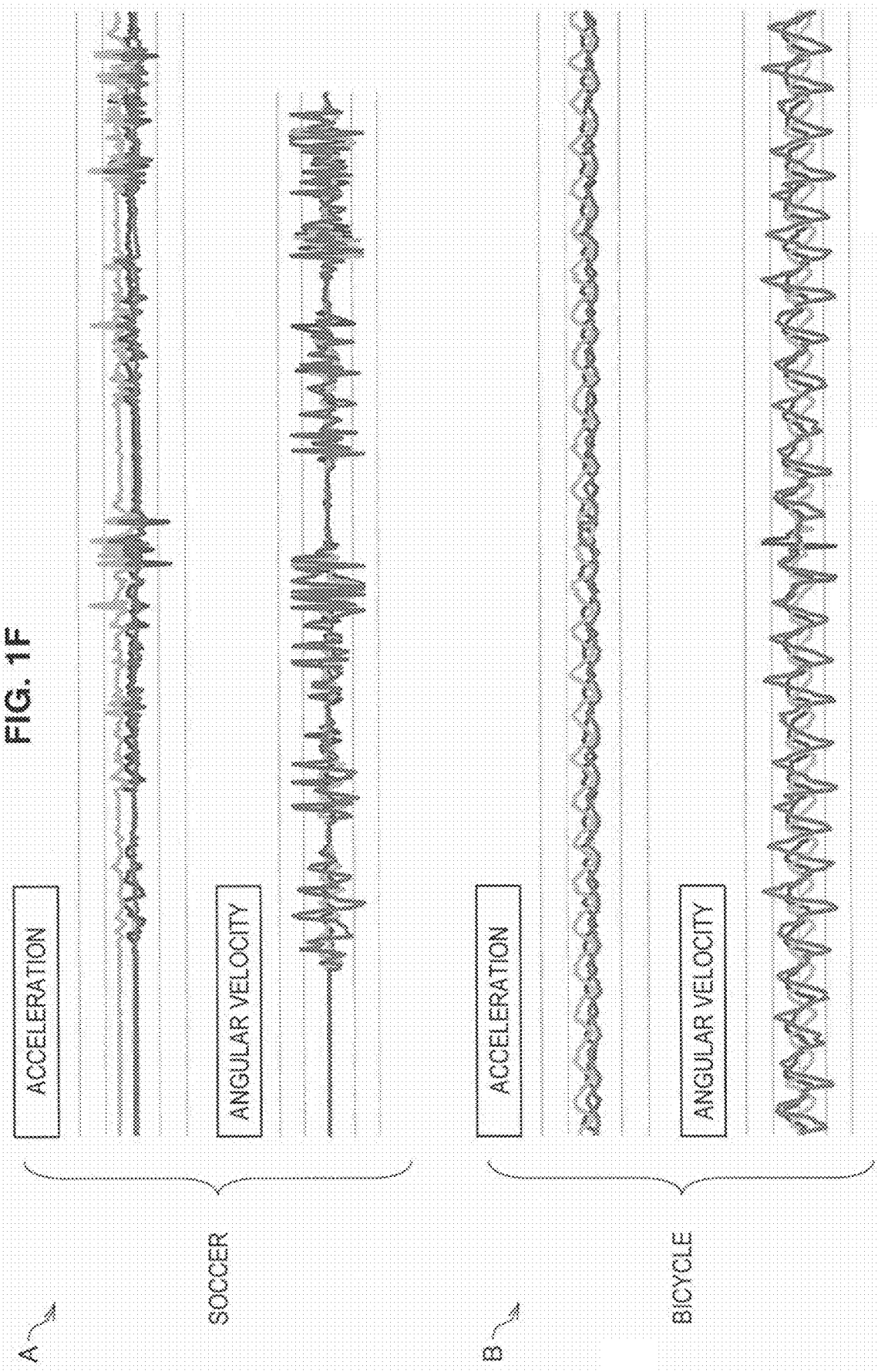
FIG. 1F is a diagram illustrated to describe an information processing method according to the present embodiment.

Hereinafter, (a) preferred embodiment(s) of the present disclosure will be described in detail with reference to the appended drawings. In this specification and the drawings, elements that have substantially the same function and structure are denoted with the same reference signs, and repeated explanation is omitted.

The description will be given in the following order.
1. Information Processing Method according to present Embodiment
2. Information Processing Apparatus according to present Embodiment
3. Program according to present Embodiment
(Information Processing Method According to Present Embodiment)

Prior to the description of an information processing apparatus according to the present embodiment, an information processing method according to the present embodiment will be first described. The information processing method according to the present embodiment will be described by taking the case in which the information processing apparatus according to the present embodiment performs a process of implementing the information processing method according to the present embodiment as an example.

As described above, for example, when recognition for user's behavior is performed simply using values detected by a sensor. The technique of recognizing the user's behavior depending on the position at which a device including a sensor (or device to which an external sensor is attached, and this is similarly applied to the following description) is worn by the user has low accuracy. Further, even it is likely to be failed to recognize the user's behavior.

FIGS. 1A to 1H are diagrams illustrated to describe the information processing method according to the present embodiment. FIGS. 1A to 1H illustrate an example of a detection value of a sensor depending on a wearing position and user's behavior in a sensor-equipped device including an acceleration sensor and a gyro sensor.

More specifically, FIG. 1A illustrates an example of detection values in a case where a sensor-equipped device is worn on the head of the user. The portion A of FIG. 1A shows detection values in a case where a user is swimming. The portion B of FIG. 1A shows detection values in a case where the user is nodding.

In addition, FIG. 1B illustrates an example of detection values in a case where the sensor-equipped device is worn on the jaw of the user. The portion A of FIG. 1B shows detection values in a case where the user speaks with his voice. The portion B of FIG. 1B shows detection values in a case where the user is chewing.

In addition, FIG. 1C illustrates an example of detection values in a case where the sensor-equipped device is worn around the neck of the user. The portion A of FIG. 1C shows detection values in a case where the user is squatting. The portion B of FIG. 1C shows detection values in a case where the user performs push-ups. In addition, FIG. 1D illustrates an example of detection values in a case where the sensor-equipped device is worn around the neck of the user. The portion A of FIG. 1D shows detection values in a case where the user performs an abdominal muscle exercise. The portion B of FIG. 1D shows detection values in a case where the user performs a back extension exercise.

In addition, FIG. 1E illustrates an example of detection values in a case where the sensor-equipped device is worn on the chest of the user and shows detection values in a case where the user is breathing.

In addition, FIG. 1F illustrates an example of detection values in a case where the sensor-equipped device is worn on the ankle of the user. The portion A of FIG. 1F shows detection values in a case where the user is playing soccer. The portion B of FIG. 1F shows detection values in a case where the user rides in a bicycle.

In addition, FIG. 1G illustrates an example of detection values in a case where the sensor-equipped device is worn on the finger of the user and shows detection values in a case where the user is typing.

In addition, FIG. 1H illustrates an example of detection values in a case where the sensor-equipped device is worn on the wrist of the user. The portion A of FIG. 1H shows detection values in a case where the user is making a tennis swing. The portion B of FIG. 1H shows detection values in a case where the user is making a baseball swing.

The sensor-equipped device, when being worn by the user, a detection value is obtained, for example, as shown in FIGS. 1A to 1H.

For example, when a detection value of the acceleration sensor in the case of swimming as shown in the portion A of FIG. 1A and a detection value of the acceleration sensor in the case of squatting as shown in the portion A of FIG. 1C are referred, the detection values of the acceleration sensors are similar. Thus, when the behavior recognition of the user is performed simply by using the detection value of the sensor, it is difficult to determine whether the user is swimming or is squatting, or even an erroneous determination result may be obtained.

In addition, when the sensor-equipped device is worn on the jaw of the user, the fluctuation in detection values of the sensor is significantly smaller than that obtained in the case where the sensor-equipped device is worn on the user's head or around the user's neck, for example as shown in FIG. 1B. In other words, for example, when the sensor-equipped device is worn on the user's jaw, the user's behavior is necessary to be recognized upon the detection of minute vibration. Thus, it is desirable to change settings of resolution of the sensor, for example depending on the position at which the sensor-equipped device is placed on the user, thereby more accurately detecting the behavior of the user who wears the sensor-equipped device.

Thus, the information processing apparatus according to the present embodiment performs, for example, (1) behavior recognition mode setting process, (2) behavior recognition process, and (3) execution control process, which will be described later, as a process of implementing the information processing method according to the present embodiment. This allows the user's behavior to be recognized with higher accuracy and allows a process depending on the recognized behavior of the user to be controlled.

(1) Behavior Recognition Mode Setting Process

The information processing apparatus according to the present embodiment sets a behavior recognition mode based on wearing position information on a setting target device.

In this connection, the wearing position information according to the present embodiment is data indicating the wearing position at which a setting target device is worn by the user. The wearing position information according to the present embodiment may be data that directly indicates the wearing position (e.g., data indicating the wearing position using a character string) such as head and neck or may be data that indirectly indicates the wearing position (e.g., an ID indicating the wearing position).

The wearing position information according to the present embodiment is generated by the information processing apparatus according to the present embodiment that performs (4) wearing position recognition process, which will be described later. When the information processing apparatus according to the present embodiment generates the wearing position information, the information processing apparatus according to the present embodiment performs the process of implementing the information processing method according to the present embodiment by using the generated wearing position information.

In addition, the wearing position information according to the present embodiment may be generated in an external device that performs a process similar to (4) wearing position recognition process that will be described later. When the wearing position information is generated by the external device, the information processing apparatus according to the present embodiment acquires wearing position information from the external device through communication, for example, via a communication unit (described later) or an external communication device connected thereto, and performs the process of implementing the information processing method according to the present embodiment by using the acquired wearing position information.

In addition, the setting target device according to the present embodiment is the device to be a target to which the behavior recognition mode is set. Examples of the setting target device according to the present embodiment include a device in which a sensor used to recognize user's behavior is installed and a device to which an external sensor for recognition of user's behavior is attached. The setting target device according to the present embodiment may be the information processing apparatus according to the present embodiment or may be an external device of the information processing apparatus according to the present embodiment.

Specifically, examples of the setting target device according to the present embodiment include a device capable of being directly worn on the user's body and a device capable of being indirectly worn by placing it into the thing including a bag and a pocket that can be directly worn by the user, such as "portable device including smartphone, mobile phone, or tablet device" and "wearable device".

The following description will be given by taking an example in which the setting target device according to the present embodiment is a wearable device.

Figure 2:
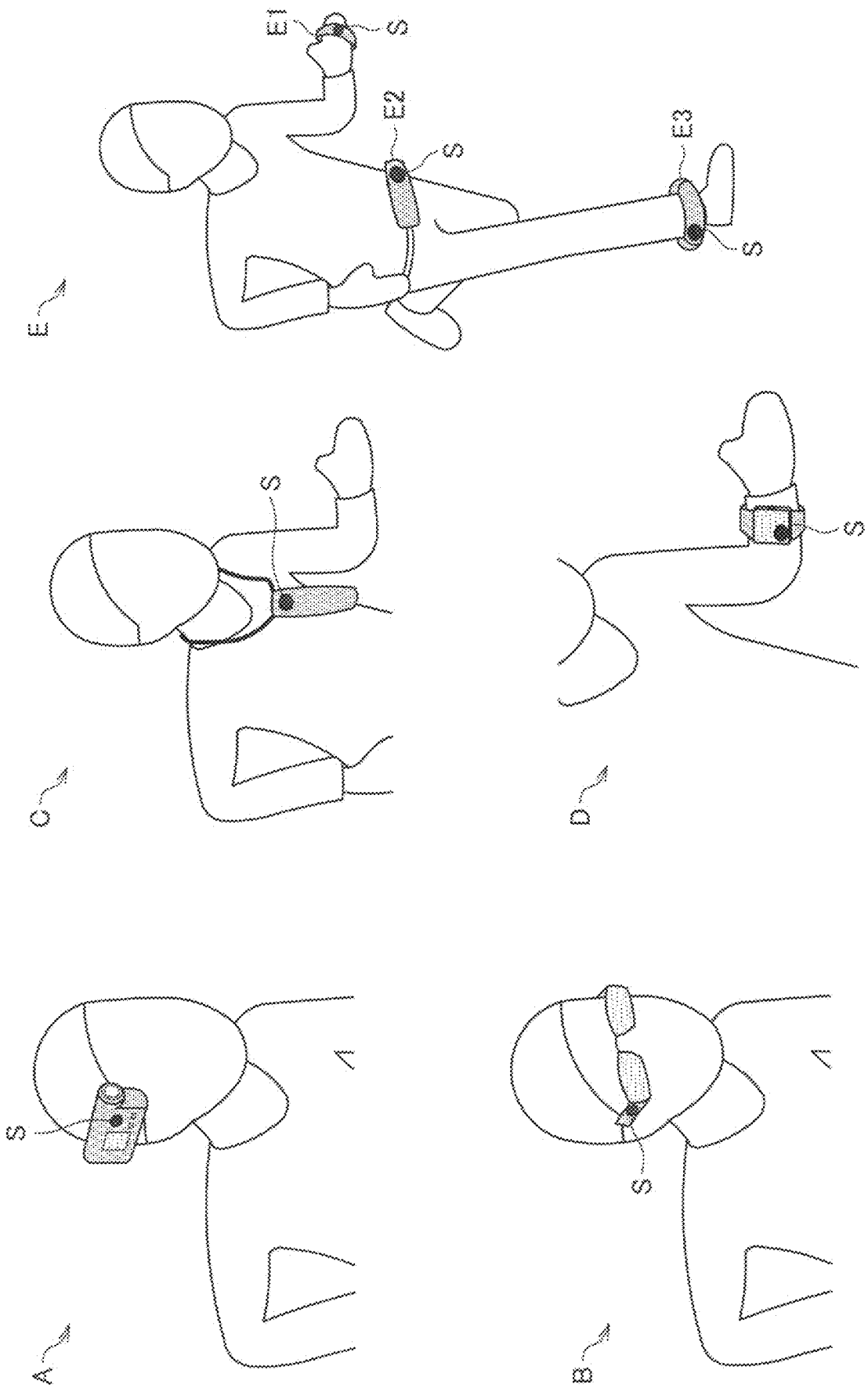
FIG. 2 is a diagram illustrated to describe an example of a setting target device according to the present embodiment.

FIG. 2 is a diagram illustrated to describe an example of the setting target device according to the present embodiment, and illustrates an example of a wearable device in a case where the setting target device according to the present embodiment is the wearable device. The portions A to E shown in FIG. 2 show an example of the respective wearable devices.

As illustrated in FIG. 2, examples of the wearable device according to the present embodiment include the following devices as the wearable device being capable of serving as the setting target device according to the present embodiment. Of course, the wearable device according to the present embodiment is not limited to the following examples.

Head-mounted device (portion A in FIG. 2): head-mounted display (HMD) and imaging device as an example Eyewear device (portion B in FIG. 2): HMD and glasses device as an example Neck-worn device (portion C in FIG. 2): imaging device, headset, necklace-shaped device, and data logger, as an example Wrist/arm-worn device (portion D in FIG. 2): wristwatch device, data logger, bracelet device, and wristband device, as an example Hand/finger-worn device (portion E1 in FIG. 2): glove-shaped device and ring-shaped device as an example Waist/jacket/pocket-worn device (portion E2 in FIG. 2): belt apparatus, clip/refrigerator magnet type device and data logger as an example Ankle/leg-worn device (portion E3 in FIG. 2): anklet device and data logger as an example In addition, each of the wearable devices has a sensor S used for behavior recognition. The sensor S used for behavior recognition may be a sensor that is incorporated in the wearable device (device included in the wearable device) or may be an external sensor connected to the wearable device.

In some cases, a sensor used for behavior recognition corresponding to the setting target device, like the sensor S used for behavior recognition for example shown in FIG. 2, is described as "sensor corresponding to the setting target device" hereinafter.

Examples of the sensor according to the present embodiment include an acceleration sensor, global positioning system (GPS) device, gyro sensor, atmospheric pressure sensor, proximity sensor, and biosensor. Note that, the sensor according to the present embodiment is not limited thereto. The sensor may be any sensor that can be used in a process for recognition of user's behavior, such as the behavior recognition process according to the present embodiment.

The behavior recognition mode according to the present embodiment is a mode for deciding a status of behavior. The behavior recognition mode indicates a single setting relating to the behavior recognition, or a combination of a plurality of settings relating to the behavior recognition.

Examples of the behavior recognition mode according to the present embodiment include one or a combination of both of "sensor-related setting" and "setting relating to process for behavior recognition".

Examples of the sensor-related setting according to the present embodiment include one or both of a setting of the type of a sensor used for behavior recognition and a setting of a parameter of a sensor used for behavior recognition (e.g., sampling setting and single mode setting). Examples of the setting of the type of a sensor used for behavior recognition include a setting of a sensor being operated (capable of including a setting of turning power of the sensor being not operated off). In addition, examples of the setting of a parameter of a sensor used for behavior recognition include any setting relating to the operation of a sensor or the output of detection value of a sensor such as sampling setting and sensing mode setting.

In addition, examples of the setting relating to process for behavior recognition according to the present embodiment include one or more of a setting of a type of feature amount used for behavior recognition, a setting of algorithms used in a process for behavior recognition, and a setting of model data used in a process for behavior recognition, among detection values of a sensor corresponding to a setting target device.

The information processing apparatus according to the present embodiment can recognize the wearing position at which the setting target device is worn by the user by referring to the wearing position information. The information processing apparatus according to the present embodiment sets a behavior recognition mode corresponding to the recognized wearing position with respect to the setting target device.

The information processing apparatus according to the present embodiment specifies a behavior recognition mode corresponding to the recognized wearing position, for example by the use of a table (or database) in which the wearing position is associated with a behavior recognition mode to be set and the wearing position recognized on the basis of the wearing position information. Then, the information processing apparatus according to the present embodiment sets the specified behavior recognition mode with respect to the setting target device.

A method of specifying the behavior recognition mode according to the present embodiment is not limited thereto.

For example, when there are a plurality of behavior recognition modes corresponding to the wearing position, the information processing apparatus according to the present embodiment can specify a behavior recognition mode corresponding to the wearing position, by using one or more of a history of the set behavior recognition mode, time, and a position of a setting target device corresponding to wearing position information.

In addition, when there are a plurality of behavior recognition modes corresponding to the wearing position, the information processing apparatus according to the present embodiment presents a behavior recognition mode as a candidate to be set to the user of the setting target device visually and/or acoustically, and the behavior recognition mode selected by the user may be specified as a behavior recognition mode corresponding to the wearing position.

Examples of the behavior recognition mode corresponding to the wearing position include a behavior recognition mode corresponding to the user's behavior described below. It will be understood that the behavior recognition mode corresponding to the wearing position according to the present embodiment is not limited to the behavior recognition mode corresponding to the user's behavior described below.

Case where wearing position is "head": recognition of swimming (e.g., swimming style and number of turns) and recognition of nodding Case where wearing position of "jaw": recognition of whether to speak, recognition of number of chewing times, and recognition of food type Case where wearing position of "neck": recognition of training (e.g., squat and push-ups)

Case where wearing position of "chest": recognition of whether to breathe (body movement)

Case where wearing position of "ankle": recognition of soccer (e.g., soccer kick motion) and recognition of bicycle cadence Case where wearing position of "finger": recognition of typing Case where wearing position of "wrist": recognition of swing (e.g., baseball, tennis, and golf)

Case where wearing position of "trouser pocket": recognition of vehicle (e.g., train and bus)

More specifically, as the process for behavior recognition mode setting by the information processing apparatus according to the present embodiment, for example, processes of the following items (1-1) and (1-2) are performed.

(1-1) First Example of Process for Behavior Recognition Mode Setting: Execution of Sensor-Related Setting The information processing apparatus according to the present embodiment performs the sensor-related setting based on the wearing position information with respect to a sensor corresponding to the setting target device.

More specifically, for example, when the setting target device is an external device of the information processing apparatus according to the present embodiment, the information processing apparatus according to the present embodiment causes the setting target device to perform the sensor-related setting, for example, by transmitting data indicating the sensor-related setting to the setting target device. For example, the information processing apparatus according to the present embodiment causes a communication unit (described later) included in the information processing apparatus according to the present embodiment or an external communication device connected to the information processing apparatus according to the present embodiment to transmit data indicating the sensor-related setting.

Examples of the data indicating the sensor-related setting according to the present embodiment include one or both of the following data. Note that, the data indicating the sensor-related setting according to the present embodiment is not limited to the following examples. Examples of the data indicating the sensor-related setting according to the present embodiment include any data (or data group) capable of controlling operation of the sensor.

Data indicating types of sensors to be activated (for example, sensor ID)

Data indicating parameters of the sensor

In addition, the data indicating the sensor-related setting according to the present embodiment may include an instruction to perform execution of the sensor-related setting, as an example.

In addition, when the setting target device is its own device (information processing apparatus according to the present embodiment), the information processing apparatus according to the present embodiment performs the sensor-related setting with respect to a sensor (an example of a sensor corresponding to the setting target device) that constitutes a detection unit (described later) included therein or an external sensor (an example of a sensor corresponding to the setting target device) connected thereto.

(1-2) Second Example of Process for Behavior Recognition Mode Setting: Execution of Setting Relating to Process for Behavior Recognition The information processing apparatus according to the present embodiment performs the setting relating to process for behavior recognition based on the wearing position information.

The information processing apparatus according to the present embodiment performs the setting relating to process for behavior recognition, for example, by associating the data indicating the setting target device with the data indicating the setting relating to process for behavior recognition corresponding to the wearing position recognized based on the wearing position information and by recording them in a table, a database, or the like.

Examples of the data indicating the setting target device according to the present embodiment include a device ID or the like.

An Example of the data indicating the setting relating to process for behavior recognition according to the present embodiment includes one or more of the following data. Note that, the data indicating the setting relating to process for behavior recognition according to the present embodiment is not limited to the following examples. Examples of the data indicating the setting relating to process for behavior recognition according to the present embodiment include any data (or data group) capable of controlling the process for behavior recognition.

- Data indicating types of feature amounts (for example, IDs indicating the feature amounts)
- Data indicating an algorithm used in a process for behavior recognition (for example, program data and ID indicating algorithm)
- Data indicating model data used in a process for behavior recognition (for example, model data itself, and ID indicating the model data)

The information processing apparatus according to the present embodiment refers to the table or the like and uses data indicating the setting relating to process for behavior recognition corresponding to the setting target device, thereby performing a process of item (2) (behavior recognition process) described later.

When the setting target device is an external device of the information processing apparatus according to the present embodiment and the process for behavior recognition is performed in the external device, the information processing apparatus according to the present embodiment may cause the external device to perform the process for behavior recognition, for example by transmitting the data indicating the setting relating to process for behavior recognition, which corresponds to the wearing position recognized on the basis of the wearing position information, to the external device. The information processing apparatus according to the present embodiment causes a communication unit (described later) included in the information processing apparatus according to the present embodiment or an external communication device connected to the information processing apparatus according to the present embodiment to transmit the data indicating the setting relating to process for behavior recognition.

The data indicating the setting relating to process for behavior recognition that is transmitted to the external device as the setting target device from the information processing apparatus according to the present embodiment includes, for example, an instruction to perform an instruction for causing the setting relating to behavior recognition to be performed.

The information processing apparatus according to the present embodiment sets an behavior recognition mode based on the wearing position information with respect to the setting target device, for example by performing the process according to the first example described in the above item (1-1) or the process according to the second example described in the above item (1-2).

(2) Behavior Recognition Process

The information processing apparatus according to the present embodiment recognizes user's behavior on the basis of the set behavior recognition mode and detection values of a sensor corresponding to the setting target device.

The information processing apparatus according to the present embodiment recognizes the user's behavior, for example by performing pattern matching between the feature amount extracted from the detection value of a sensor in accordance with the set behavior recognition mode and the feature amount corresponding to the recognized candidate's behavior.

The behavior recognition process according to the present embodiment is not limited thereto. For example, the information processing apparatus according to the present embodiment may recognize the user's behavior by using any technique capable of recognizing the user's behavior on the basis of the detection value of a sensor, such as a process using threshold processing.

Examples of the user's behavior recognized in the behavior recognition process according to the present embodiment include respective user's behaviors corresponding to FIGS. 1A to 1H and user's behavior described in the example of the user's behavior described above such as recognition of swimming.

The information processing apparatus according to the present embodiment can recognize the same user's behavior in a plurality of wearing positions. Examples of the user's behavior that can be recognized in the plurality of wearing positions include the "recognition of vehicle" that recognizes the user riding in a vehicle such as a train or bus, as an example.

In this connection, when the same user's behavior is recognized in a plurality of wearing positions, the process for recognition of user's behavior may be different for each wearing position. For example, a recognition model of behavior or a dictionary used for behavior recognition may be set for each wearing position, and thus the process for recognition of user's behavior can be different for each wearing position. In addition, when the same user's behavior is recognized in a plurality of wearing positions, it is also possible to perform a predetermined process that is set as the process for recognition of user's behavior, irrespective of wearing positions.

As described above, in some cases, the detection values obtained from acceleration sensors (an example of a sensor corresponding to the setting target device), including the detection value of the acceleration sensor when swimming is performed as shown in the portion A of FIG. 1A and the detection value of the acceleration sensor when a squat is performed as shown in the portion A of FIG. 1C, are similar.

The information processing apparatus according to the present embodiment sets the behavior recognition mode based on the wearing position information in the process of the above item (1) (behavior recognition mode setting process), and thus it is possible to enhance the accuracy for recognition of the user's behavior in accordance with the setting depending on the wearing position.

In addition, as described above, when the sensor-equipped device is worn on the jaw of the user, it is necessary to recognize the user's behavior upon detection of a minute vibration. The information processing apparatus according to the present embodiment sets the behavior recognition mode based on the wearing position information in the process of the above item (1) (behavior recognition mode setting process), and thus it is necessary to switch the setting of resolution of a sensor or other settings depending on the wearing position. Thus, the information processing apparatus according to the present embodiment can recognize the user's behavior with high accuracy on the basis of the detection value of the sensor corresponding to the setting target device.

(3) Execution Control Process

The information processing apparatus according to the present embodiment controls the execution of a process corresponding to the recognized user's behavior. The information processing apparatus according to the present embodiment may control the execution of a process corresponding to the wearing position indicated by the wearing position information and the recognized user's behavior. The process controlled by the execution control process according to the present embodiment is referred to as "process corresponding to behavior" hereinafter.

The information processing apparatus according to the present embodiment specifies the process corresponding to behavior, on the basis of a table (or database) in which the user's behavior is associated with a process of a control target and the user behavior recognized in the process of the above item (2) (behavior recognition process). In addition, the information processing apparatus according to the present embodiment can also specify a process corresponding to behavior, as an example, on the basis of a table (or database) in which a wearing position, user's behavior, and the process of control target are associated with each other, a wearing position indicated by the wearing position information, and the user's behavior recognized in the process of the above item (2) (behavior recognition process).

Then, when a device that executes the process corresponding to behavior is an external device of the information processing apparatus according to the present embodiment, the information processing apparatus according to the present embodiment transmits a processing instruction for performing a process corresponding to the specified behavior to the external device. The external device, when receiving the processing instruction for performing the process corresponding to behavior, executes a process corresponding to behavior in accordance with the processing instruction.

In addition, the information processing apparatus according to the present embodiment may transmit data relating to the process corresponding to the specified behavior (e.g., an application used for execution of the process and processing parameters) to the external device. The information processing apparatus according to the present embodiment causes a communication unit (described later) included in the information processing apparatus according to the present embodiment or an external communication device connected to the information processing apparatus according to the present embodiment to transmit the processing instruction for performing a process corresponding to behavior.

In addition, when the device that executes the process corresponding to behavior is its own device (information processing apparatus according to the present embodiment), the information processing apparatus according to the present embodiment executes a process corresponding to the specified behavior.

The information processing apparatus according to the present embodiment controls the execution of the process corresponding to behavior by causing the external device to perform the process corresponding to behavior as described above or by performing the process corresponding to behavior, as an example.

A specific example of the execution control process will be described hereinafter by mainly taking a case where the device that executes the process corresponding to behavior is a wearable device (an example of the setting target device) as an example. In addition, a specific example of the execution control process will be described hereinafter by mainly taking a case where the information processing apparatus according to the present embodiment controls the execution of the process corresponding to the wearing position indicated by the wearing position information and the recognized user's behavior, as an example. It will be understood that the execution control process according to the present embodiment is not limited to examples described below.

(a) First Example of Execution Control Process: Case where Wearing Position is "Neck"

In the process of the above item (2) (behavior recognition process), when the recognition of a training such as a squat or push-ups is performed, the information processing apparatus according to the present embodiment specifies a "process of activating an application of giving an encouragement with voice" as the process corresponding to behavior, as an example. Then, the information processing apparatus according to the present embodiment causes a wearable device worn by the user to output sounds.

When the wearing position of the wearable device is the neck, information may be presented to the user by displaying a text, an image, or the like on a display screen of the wearable device. Even in this case, the contents to be presented to the user are less likely to be conveyed to the user who wears the wearable device. Thus, information processing apparatus according to the present embodiment conveys information to the user who wears the wearable device by causing the wearable device to output sounds.

In this connection, the information processing apparatus according to the present embodiment may cause an application for reading out the number of training sessions with voice of a particular celebrity or advertising character to activate the wearable device worn by the user.

(b) Second Example of Execution Control Process: Case where Wearing Position is "Chest"

In the process of the above item (2) (behavior recognition process), when the recognition of whether to breathe is performed, the information processing apparatus according to the present embodiment specifies a "process of activating an application capable of sharing the pace of breathing with a friend" as the process corresponding to behavior, as an example. Then, the information processing apparatus according to the present embodiment causes a wearable device worn by the user to activate the application capable of sharing the pace of breathing with a friend.

In this connection, the application capable of sharing the pace of breathing with a friend has a function of adding the pace of breathing to a behavior status or a function of controlling an avatar (e.g., producing more sweat on the avatar when breathing heavily from running, flushing cheeks when breathing heavily at rest, or the like).

The application that shares the pace of breathing with a friend may have a function of sharing data between devices in which the same application is being activated in a range over which the wearable device can communicate, as an example. When the function of sharing data is provided, for example, in an eyeglass-like device in which the same application is activated, the augmented reality (AR) technology or the like can be used on the face of the user wearing the wearable device, thereby implementing a superimposed display of contents of the shared data from the wearable device.

(c) Third Example of Execution Control Process: Case where Wearing Position is "Chest"

In the process of the above item (2) (behavior recognition process), when the recognition of whether to breathe during sleep is performed, the information processing apparatus according to the present embodiment specifies a "process of activating an application for checking sleep apnea syndrome" as the process corresponding to behavior, as an example. Then, the information processing apparatus according to the present embodiment causes a wearable device worn by the user to activate the application for checking sleep apnea syndrome.

The process for sleep determination may be performed in the information processing apparatus according to the present embodiment, or an external device performs the process for sleep determination and the information processing apparatus according to the present embodiment may use a result obtained by the process of sleep determination performed in the external device.

The application for checking sleep apnea syndrome has a function of detecting the condition of sleep apnea syndrome by using both the result of sleep determination and the result of breath determination, as an example. In addition, when the condition of sleep apnea syndrome is detected, the application for checking sleep apnea syndrome may have a function of issuing a warning to the registered user such as the user itself or family.

(d) Fourth Example of Execution Control Process: Case where Wearing Position is "Ankle"

In the process of the above item (2) (behavior recognition process), when the recognition of soccer is performed, the information processing apparatus according to the present embodiment specifies a "process for a soccer enhancing function" as the process corresponding to behavior, as an example. Then, the information processing apparatus according to the present embodiment causes a wearable device worn by the user to execute the process for a soccer enhancing function.

Examples of the process for a soccer enhancing function according to the present embodiment include processes described below.

Process of estimating the degree of fatigue from a running distance or movement and for outputting light with a color depending on the estimation result by the wearable device worn on the ankle: the light to be outputted can be used as a goal set by a director's strategy or as a reference of a strategy established by a player.

Process of presenting the strength of a kick speed or impact with sound by the wearable device worn on the ankle (e.g., "smack" (weaker case) and "thump" (stronger case)): information is extended in watching a game by presenting the strength of a kick speed or the like with sound, and thus it is possible to watch a game and make it more enjoyable.

(e) Fifth Example of Execution Control Process: Case where Wearing Position is "Ankle"

In the process of the above item (2) (behavior recognition process), when the recognition of bicycle cadence is performed, the information processing apparatus according to the present embodiment specifies a "process relating to cycling function or a process relating to training function" as the process corresponding to behavior, as an example. Then, the information processing apparatus according to the present embodiment determines a process of specifying by the cadence. Then, the information processing apparatus according to the present embodiment causes a wearable device worn by the user to execute the process relating to cycling function or the process relating to training function.

Examples of the process relating to cycling function according to the present embodiment include one or both of a process of playing a song at beat per minute (BPM) in the cadence and a process of outputting navigation of cycling courses with sounds.

In addition, examples of the process relating to training function according to the present embodiment include one or both of a process of automatically generating a training menu and a process of instructing the pace and course with sounds.

(f) Sixth Example of Execution Control Process: Case where Wearing Position is "Finger"

In the process of the above item (2) (behavior recognition process), when the recognition of typing is performed, the information processing apparatus according to the present embodiment specifies a "process of providing feedback to the user (e.g., feedback using sound (including music), vibration, text, light, or the like)" as the process corresponding to behavior, as an example. Then, the information processing apparatus according to the present embodiment causes a wearable device worn by the user to execute the process of providing feedback to the user.

Examples of the process of providing feedback to the user include a process of prompting the user to take a break when the user continues typing for a predetermined time or over.

(g) Seventh Example of Execution Control Process: Case where Wearing Position is "Wrist"

In the process of the above item (2) (behavior recognition process), when the recognition of a swing of tennis, golf, baseball, or the like is performed, the information processing apparatus according to the present embodiment specifies a "process of imaging moving pictures" as the process corresponding to behavior, as an example. In addition, the information processing apparatus according to the present embodiment may further specify a "process of editing the imaged moving pictures" as the process corresponding to behavior.

The information processing apparatus according to the present embodiment causes an imaging device associated with the wearable device worn by the user to execute the process of imaging moving pictures, or causes an image processing device associated with the wearable device to execute the process of editing the imaged moving picture. The imaging device according to the present embodiment can be arranged at a position that can image the user who wears the wearable device using a tripod, as an example. The imaging device associated with the wearable device may be the same device as the image processing device associated with the wearable device.

Examples of the process of imaging an image according to the present embodiment include a process of starting the imaging of moving pictures by using a swing as a trigger and a process of terminating the imaging when a swing is not detected for the set predetermined time. As described above, by performing the process of imaging an image, it becomes possible to achieve more energy saving than a case where imaging is typically performed.

In addition, examples of the process of editing the imaged moving picture according to the present embodiment include a process of automatically generating a digest image from the imaged moving picture using termination of the imaging as a trigger.

(h) Eighth Example of Execution Control Process: Case where Wearing Position is "Trouser Pocket"

In the process of the above item (2) (behavior recognition process), when the recognition of bicycle or walking is performed, the information processing apparatus according to the present embodiment specifies a "process of notifying a way to the user" as the process corresponding to behavior, as an example. Then, the information processing apparatus according to the present embodiment causes a device that is worn indirectly in the pocket of a trouser to notify the way to the user.

Examples of the process of notifying the way to the user according to the present embodiment include one or both of a process of providing auditory feedback by outputting sounds from a speaker and a process of providing tactile feedback by vibrating a vibrator or the like. The process of notifying the way to the user according to the present embodiment is not limited thereto. For example, the process of notifying the way to the user according to the present embodiment may be a process of notifying a way to the user using any user interface (UI) that is capable of substantially performing a notification to the user from within the pocket of a trouser. The ability to perform substantially a notification to the user from within the pocket of a trouser means that a notification method in which the notification of a way to the user does not make sense is eliminated, such as a method of displaying a map or the like on a display screen by a device worn indirectly within the pocket of a trouser.

The information processing apparatus according to the present embodiment performs the processes of the first to eighth examples described in the above items (a) to (h) respectively, as the execution process according to the present embodiment.

The execution process according to the present embodiment is not limited to the examples described above. As described above, the information processing apparatus according to the present embodiment can recognize the same user's behavior in the plurality of wearing positions, such as when the user rides in a vehicle including a train and a bus, as an example.

In the process of the above item (2) (behavior recognition process), when the recognition of vehicle is performed, the information processing apparatus according to the present embodiment specifies a "process of restricting a method of notifying to user (an example of the predetermined process being set)" as the process corresponding to behavior, as an example. Then, the information processing apparatus according to the present embodiment causes a wearable device or the like to execute the process of restricting a method of notifying to user.

Examples of the process of restricting a method of notifying to user according to the present embodiment include a process of restricting an auditory notification with sounds.

The information processing apparatus according to the present embodiment performs the process of the above item (1) (behavior recognition mode setting process), the process of the above item (2) (behavior recognition process), and the process of the above item (3) (execution control process), as a process for the information processing method according to the present embodiment, as an example.

The information processing apparatus according to the present embodiment sets a behavior recognition mode based on the wearing position information in the process of the above item (1) (behavior recognition mode setting process), and the user's behavior is recognized on the basis of the set behavior recognition mode in the process of the above item (2) (behavior recognition process). In other words, the information processing apparatus according to the present embodiment can recognize the user's behavior on the basis of the behavior recognition mode corresponding to the wearing position. Thus, the information processing apparatus according to the present embodiment can recognize the user's behavior with higher accuracy on the basis of the detection value of the sensor corresponding to the setting target device.

The information processing apparatus according to the present embodiment controls the execution of the process corresponding to behavior, corresponding to the user's behavior recognized in the process of the above item (2) (behavior recognition process). This process to be executed is performed in the process of the above item (3) (execution control process).

Thus, the information processing apparatus according to the present embodiment can perform the process of the above item (1) (behavior recognition mode setting process), the process of the above item (2) (behavior recognition process), and the process of the above item (3) (execution control process), thereby recognizing the user's behavior with higher accuracy and controlling the process depending on the recognized user's behavior.

The process for the information processing method according to the present embodiment is not limited to the processes of the above items (1) (behavior recognition mode setting process) to (3) (execution control process).

(4) Wearing Position Recognition Process

As an example, it is possible for the information processing apparatus according to the present embodiment to further perform a wearing position recognition process for recognizing a wearing position at which the setting target device is worn by the user.

When the information processing apparatus according to the present embodiment performs the wearing position recognition process according to the present embodiment, the information processing apparatus according to the present embodiment sets the behavior recognition mode based on the wearing position information indicating the wearing position recognized in the wearing position recognition process according to the present embodiment in the process of the above item (1) (behavior recognition mode setting process). In addition, when the information processing apparatus according to the present embodiment performs the wearing position recognition process according to the present embodiment, the information processing apparatus according to the present embodiment controls the execution of the process based on the wearing position information indicating the wearing position recognized in the wearing position recognition process according to the present embodiment in the process of the above item (3) (execution control process).

The wearing position recognition process according to the present embodiment will be described in more detail. As described above, the wearing position recognition process according to the present embodiment described later may be performed in the external device of the information processing apparatus according to the present embodiment.

The following description will be given by taking a case where the setting target device according to the present embodiment is the external device of the information processing apparatus according to the present embodiment. As described above, the setting target device according to the present embodiment may be information processing apparatus according to the present embodiment.

(4-1) First Example of Wearing Position Recognition Process

The information processing apparatus according to the present embodiment recognizes the wearing position on the basis of the detection value of the sensor corresponding to the setting target device and conditions corresponding to a position at which the sensor corresponding to the setting target device can be worn.

The condition corresponding to a position at which the sensor corresponding to the setting target device can be worn in the present embodiment is a constraint in the detection value of the sensor, such as posture and speed, in the wearable position. The constraint may vary for each wearable position. Thus, the information processing apparatus according to the present embodiment can recognize the wearing position based on the detection value of the sensor corresponding to the setting target device by considering the constraint.

Figure 3:
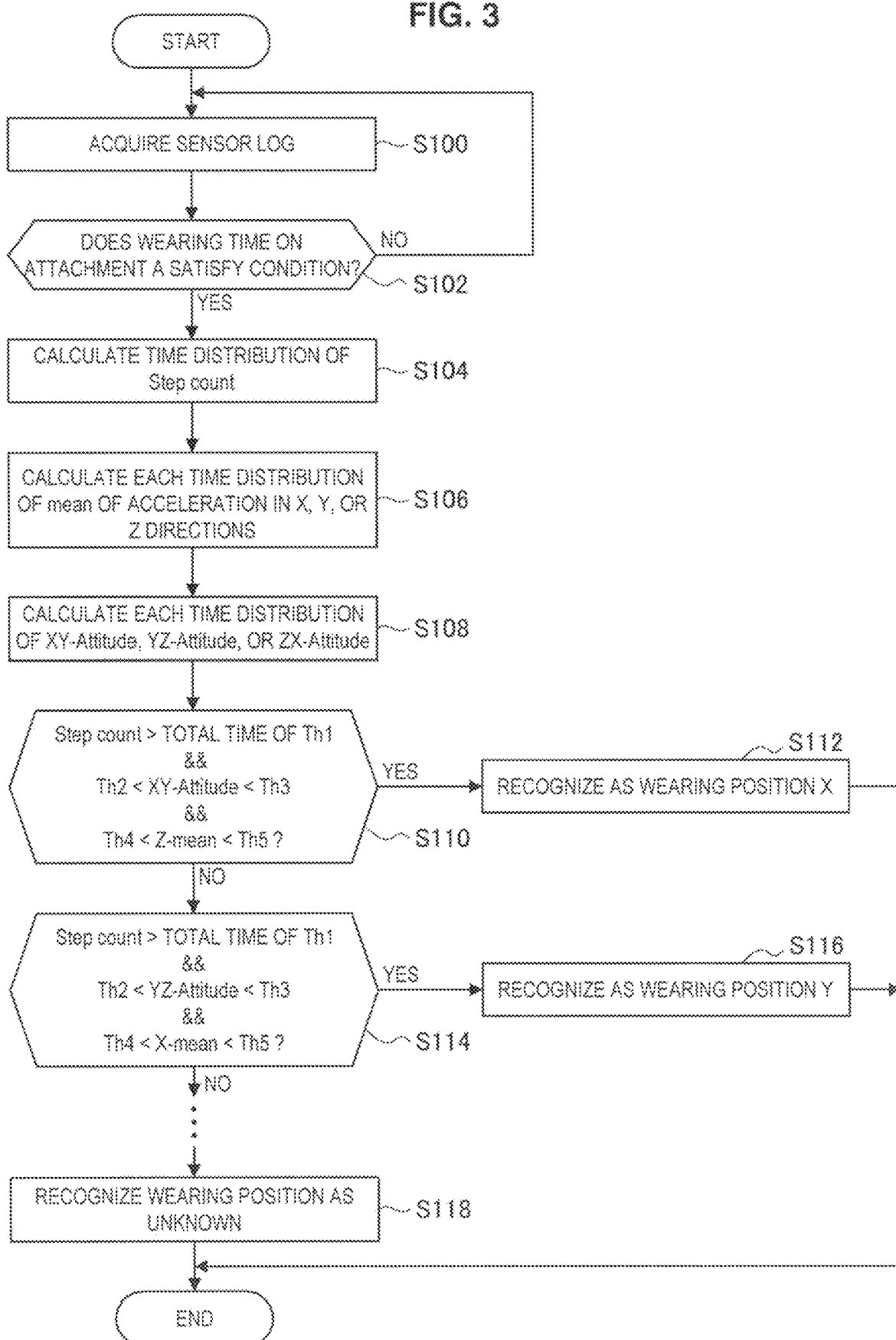
FIG. 3 is a diagram illustrated to describe a first example of a wearing position recognition process according to the present embodiment.

FIG. 3 is a diagram illustrated to describe the first example of the wearing position recognition process according to the present embodiment. FIG. 3 illustrates an example of the wearing position recognition process in a case where the setting target device having a sensor used for behavior recognition is worn on an attachment A provided in a certain wearable position.

The information processing apparatus according to the present embodiment acquires a sensor log that indicates a value detected by a sensor from the setting target device (S100). The following description will be given by taking a case where the information processing apparatus according to the present embodiment acquires a value detected by an acceleration sensor and a value detected by a gyro sensor, as a sensor log.

The information processing apparatus according to the present embodiment determines whether the wearing time on the attachment A satisfies a condition (S102). If the time elapsed after the sensor log is acquired is larger than or equal to a predetermined threshold, or if the time elapsed after the sensor log is acquired is longer than a predetermined threshold, the information processing apparatus according to the present embodiment determines that the condition is satisfied.

If it is not determined in step S102 that the condition is satisfied, the information processing apparatus according to the present embodiment performs repeatedly the process from step S100.

If it is determined in step S102 that the condition is satisfied, the information processing apparatus according to the present embodiment calculates a time distribution of Step count relating to the movement of the user who wears the setting target device (S104). In addition, the information processing apparatus according to the present embodiment calculates the time distribution of each of mean values of acceleration in X-axis, Y-axis, and Z-axis direction (S106). In addition, the information processing apparatus according to the present embodiment calculates the time distribution of each of XY-Attitude (X-axis of sensor and posture of Y-axis), YZ-Attitude (Y-axis of sensor and posture of Z-axis), and ZX-Attitude (Z-axis of sensor and posture of X-axis) (S108).

Figure 4:
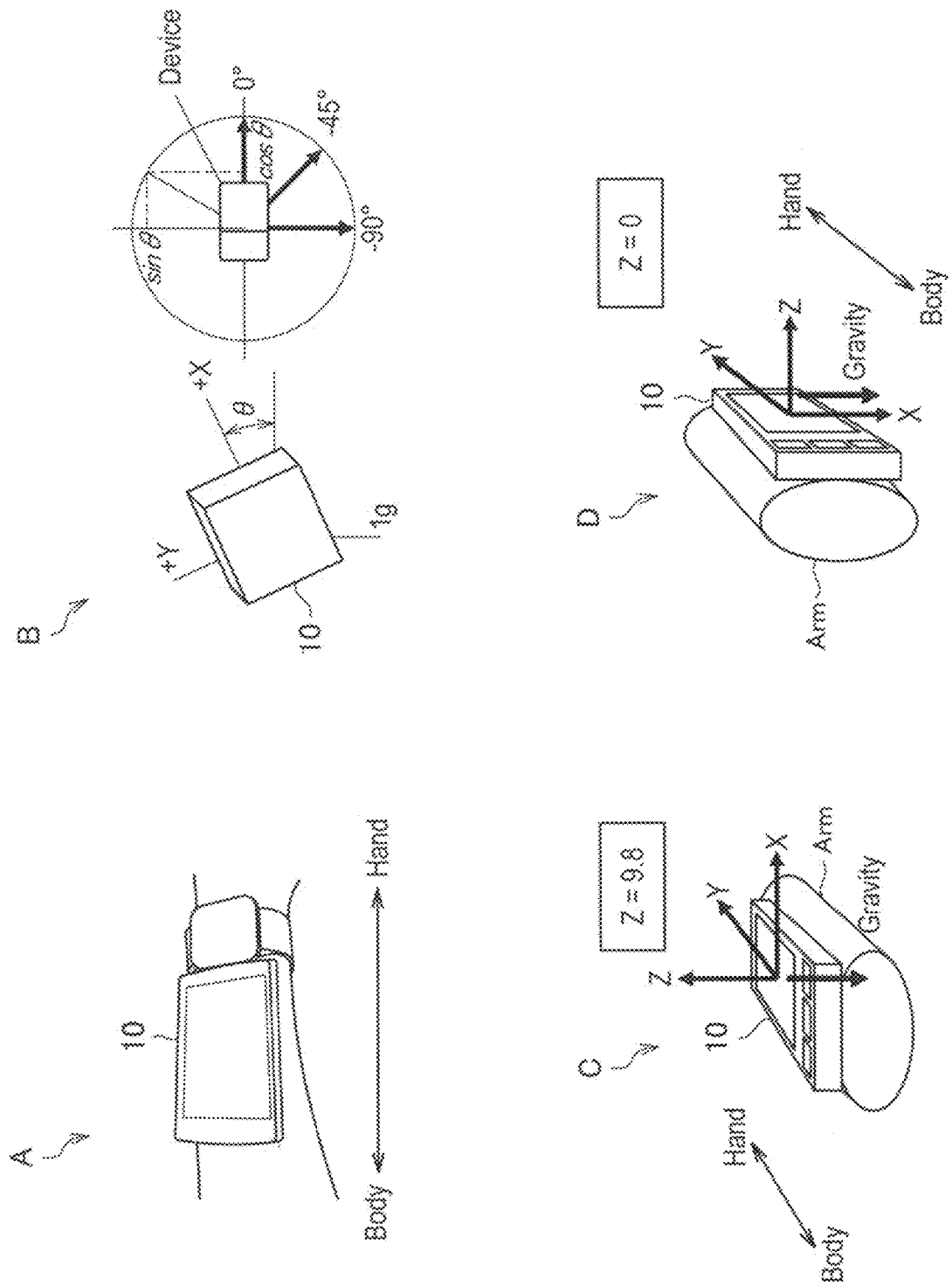
FIG. 4 is a diagram illustrated to describe a first example of a wearing position recognition process according to the present embodiment.
Figure 5:
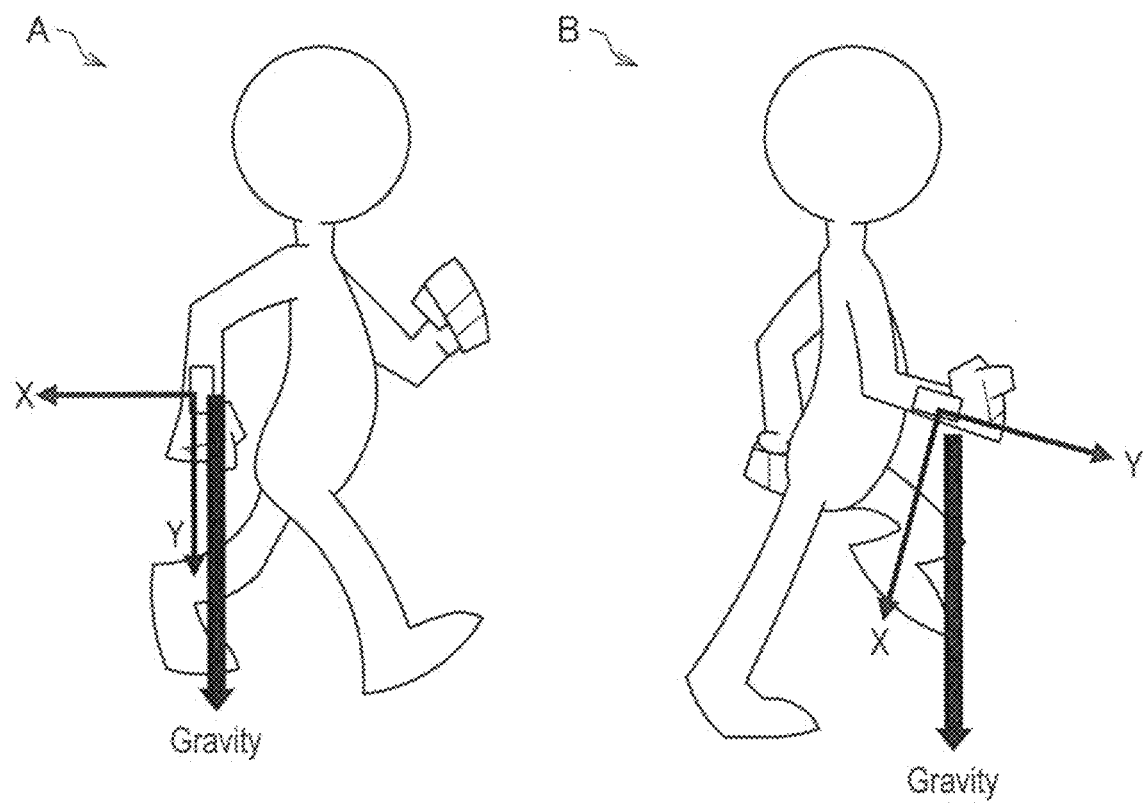
FIG. 5 is a diagram illustrated to describe a first example of a wearing position recognition process according to the present embodiment.

FIGS. 4 and 5 are diagrams illustrated to describe the first example of the wearing position recognition process according to the present embodiment, and illustrate a case where the setting target device is worn on the wrist portion of the user.

As shown in the portion A of FIG. 4, taking the setting target device 10 worn on the wrist portion of the user as an example, the XY-Attitude, YZ-Attitude, and ZX-Attitude are calculated by Equations (1) to (3), respectively. In addition, the gravity direction ("Gravity" direction shown in FIGS. 4 and 5) is calculated from the acceleration in X-axis direction ("X" direction shown in FIGS. 4 and 5) and Y-axis direction ("Y" direction shown in FIGS. 4 and 5). In addition, the acceleration in X-axis direction, Y-axis direction, and Z-axis direction ("Z" direction shown in FIGS. 4 and 5) depends on the inclination angle (theta "θ" shown in FIG. 4) in the horizontal direction.

$$XY\text{-Attitude} = \arctan(Y\text{-mean}/|X\text{-mean}|) \qquad \text{Equation (1)}$$

$$YZ\text{-Attitude} = \arctan(Z\text{-mean}/|Y\text{-mean}|) \qquad \text{Equation (2)}$$

$$ZX\text{-Attitude} = \arctan(X\text{-mean}/|Z\text{-mean}|) \qquad \text{Equation (3)}$$

The information processing apparatus according to the present embodiment recognizes the wearing position on the basis of the calculation results of steps S104 to S108 based on the detection value of the sensor corresponding to the setting target device and the condition corresponding to the wearable position ("wearing position X", "wearing position Y", . . . shown in FIG. 3) of the sensor corresponding to the setting target device (S110 to S118).

Figure 6:
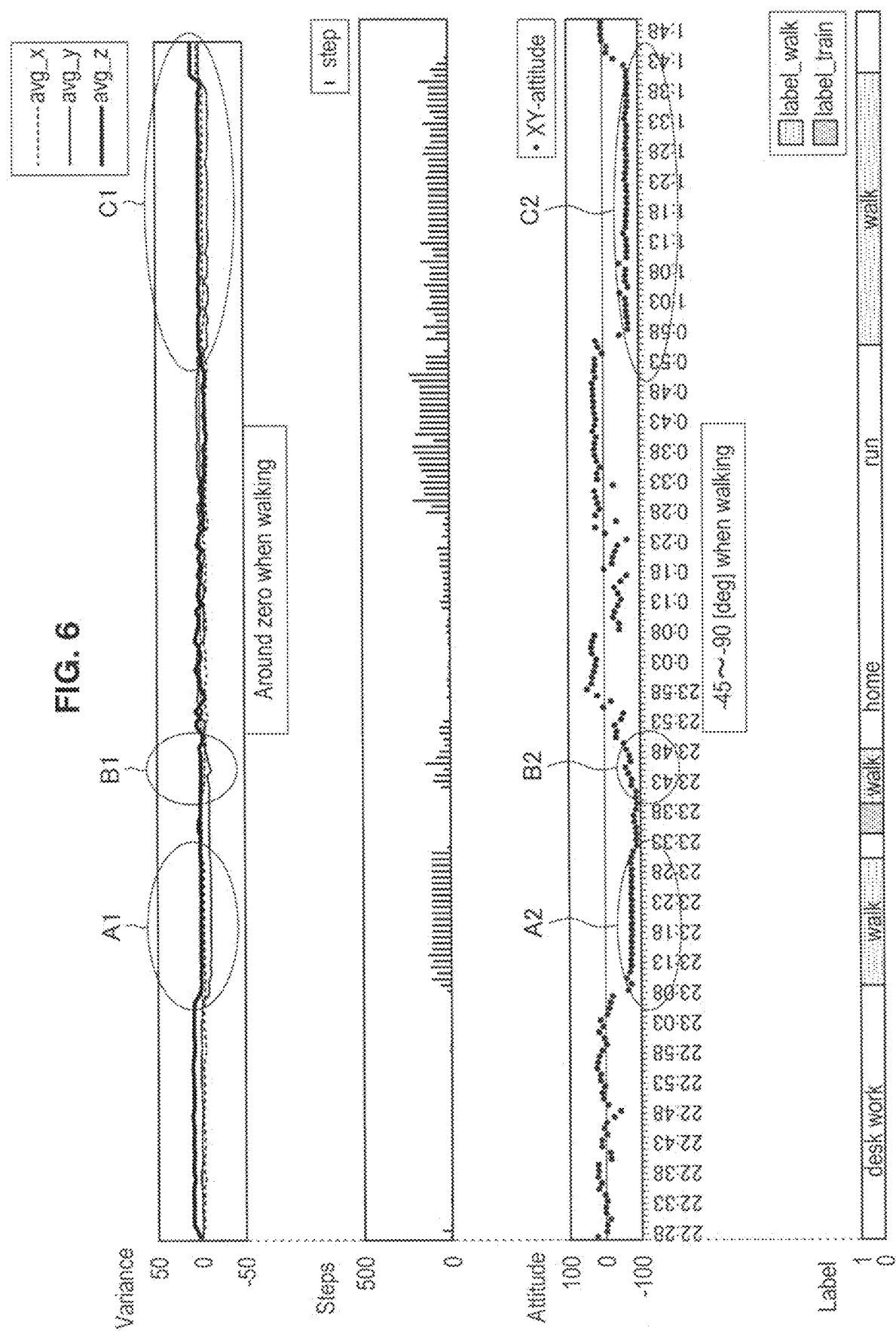
FIG. 6 is a diagram illustrated to describe a first example of a wearing position recognition process according to the present embodiment.
Figure 7:
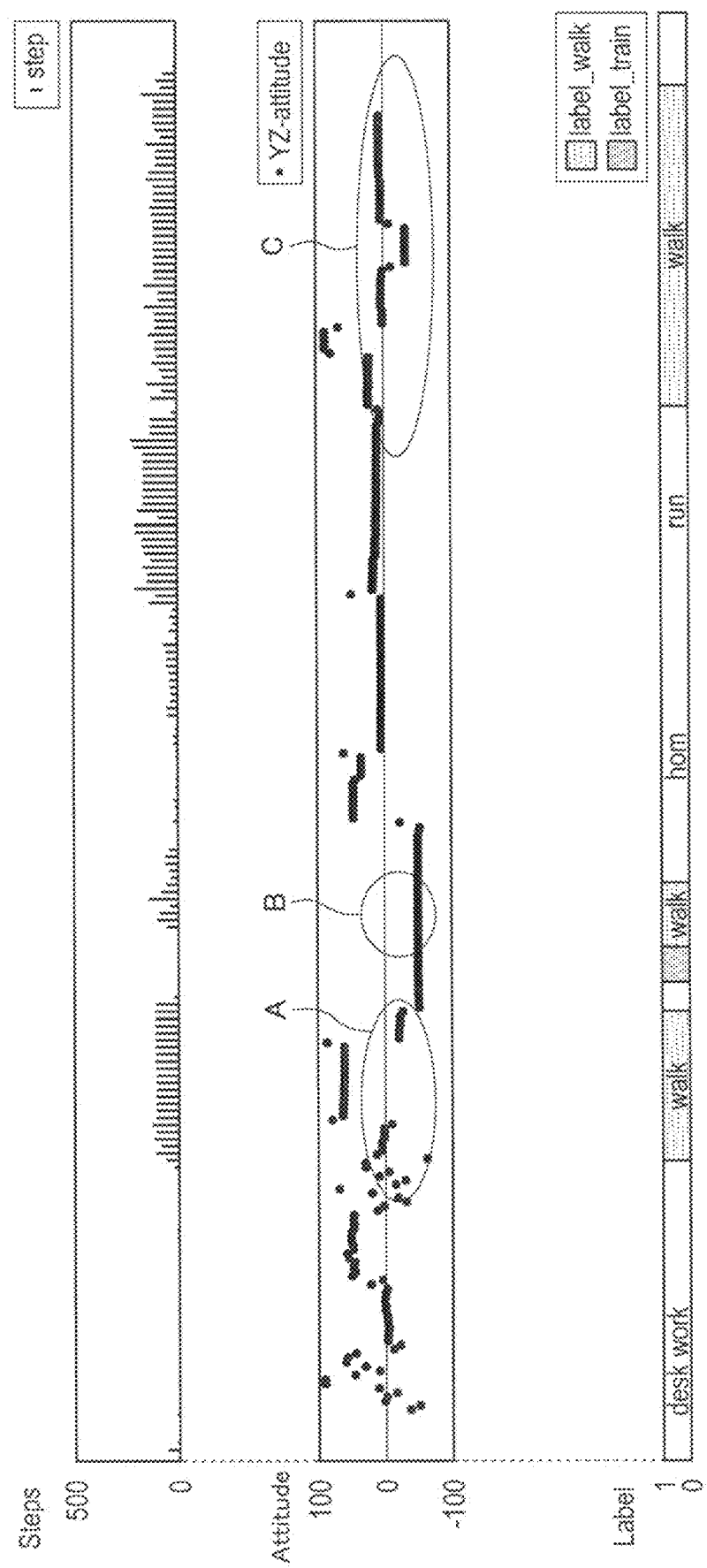
FIG. 7 is a diagram illustrated to describe a first example of a wearing position recognition process according to the present embodiment.

FIGS. 6 and 7 are diagrams illustrated to describe the first example of the wearing position recognition process according to the present embodiment. FIG. 6 illustrates an example of the calculation result of steps S104 to S108 based on the detection value of the sensor corresponding to the setting target device when the setting target device is worn on the wrist portion of the user. In addition, FIG. 7 illustrates an example of the calculation result of steps S104 to S108 based on the detection value of the sensor corresponding to the setting target device when the setting target device is worn on the waist portion of the user. In addition, the portions A1, A2, B1, B2, C1, and C2 of FIG. 6 and the portions A, B, and C of FIG. 7 illustrate illustrates an example of the calculation result of steps S104 to S108 based on the detection value of the sensor corresponding to the setting target device when the user performs walking motion.

The information processing apparatus according to the present embodiment recognizes the wearing position by performing a threshold determination corresponding to the position at which the sensor corresponding to the setting target device is wearable, as shown in steps S110 and S114 of FIG. 3, as an example.

Taking a specific example, when the wrist portion of the user is recognized as a wearing position as shown in FIG. 5, the information processing apparatus uses conditional expressions as follows.

if(steps>threshold) then(e1=TRUE)
    if(th_min<XY-attitude<th_max) then(e2=TRUE)
    if(th_min<Z-mean<th_max) then(e3=TRUE)
    if(e1×e2×e3==1) then TRUE else FALSE In addition, as shown in step S118, if the condition corresponding to the position at which the sensor corresponding to the setting target device is wearable is not satisfied, the information processing apparatus according to the present embodiment may recognize the wearing position is unknown. When the wearing position is recognized as unknown, the information processing apparatus according to the present embodiment performs a preset process (default process) in the process of the above item (1) (behavior recognition mode setting process) and the process of the above item (3) (execution control process).

(4-2) Second Example of Wearing Position Recognition Process

The information processing apparatus according to the present embodiment recognizes the wearing position on the basis of the detection value of the sensor corresponding to the setting target device and the output of a reference device to be a reference for the recognition of the wearing position.

Examples of the reference device according to the present embodiment include a sensor used for behavior recognition corresponding to the setting target device, such as an atmospheric pressure sensor, as an example. When the reference device according to the present embodiment is a sensor used for behavior recognition corresponding to the setting target device, the output of the reference device is the detection value of the sensor.

Figures 8, 9:
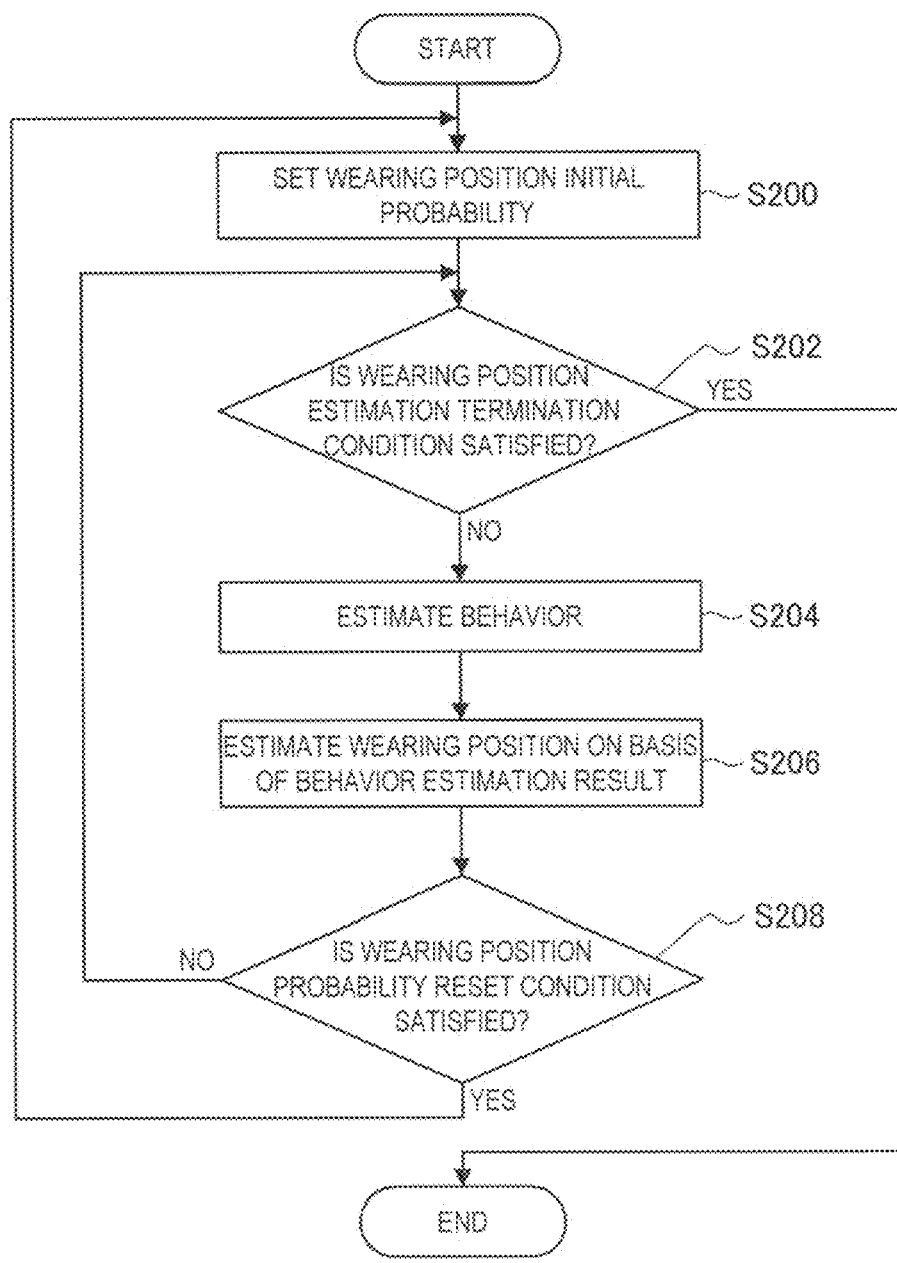
FIG. 8 is a diagram illustrated to describe a second example of a wearing position recognition process according to the present embodiment.
FIG. 9 is a diagram illustrated to describe a third example of a wearing position recognition process according to the present embodiment.

FIG. 8 is a diagram illustrated to describe a second example of the wearing position recognition process according to the present embodiment. FIG. 8 illustrates an example of a table used for recognition of a wearing position when the reference device is an atmospheric pressure sensor that is worn on the waist portion of the user and a sensor that is wearable on each portion of the user and is used for behavior recognition corresponding to the setting target device includes an atmospheric pressure sensor.

The information processing apparatus according to the present embodiment subtracts the detection value of the atmospheric pressure sensor that is worn on the waist portion to be the output of the reference device from the detection value of the sensor corresponding to the setting target device, as an example. The wearing position that corresponds to the subtracted value is specified in the table shown in FIG. 8, and the specified wearing position is recognized as the wearing position.

The reference device according to the present embodiment is not limited to the sensor used for behavior recognition corresponding to the setting target device. For example, the reference device according to the present embodiment may be a device other than sensors used for behavior recognition corresponding to the setting target device, such as audio output device including a speaker. When the reference device according to the present embodiment is an audio output device, the output of the reference device is an audio signal outputted from the audio output device, as an example.

For example, when the reference device according to the present embodiment is an audio output device, examples of the sensor used for behavior recognition corresponding to the setting target device include an audio input device such as a microphone. The information processing apparatus according to the present embodiment specifies a phase difference between an audio signal outputted from the audio output device as the reference device and an audio signal detected in the audio input device. The information processing apparatus according to the present embodiment recognizes the wearing position corresponding to the specified phase difference by using the table in which the phase difference and the wearing position are associated with each other, which is similar to FIG. 8, as an example.

In the case where the reference device according to the present embodiment is a device other than the sensor used for behavior recognition corresponding to the setting target device, the reference device according to the present embodiment and the sensor used for behavior recognition corresponding to the setting target device are not limited to a device related to the audio signal. The reference device according to the present embodiment and the sensor used for behavior recognition corresponding to the setting target device in the above case may be any device that can recognize a wearing position using the signal phase difference.

(4-3) Third Example of Wearing Position Recognition Process

The information processing apparatus according to the present embodiment estimates the wearing position and recognizes the estimated wearing position as the wearing position, on the basis of "estimation result of user's behavior estimated on the basis of the detection value of the sensor corresponding to the setting target device".

FIG. 9 is a diagram illustrated to describe a third example of the wearing position recognition process according to the present embodiment.

The information processing apparatus according to the present embodiment sets a wearing position initial probability (S200).

FIG. 10 is a diagram illustrated to describe the third example of the wearing position recognition process according to the present embodiment. The portion A of FIG. 10 illustrates an example of the wearing position initial probability, and the portion B of FIG. 10 illustrates an example of the updated wearing position initial probability as a result of performing the process in step S204 of FIG. 9 described later.

The information processing apparatus according to the present embodiment sets the wearing position initial probability by reading data in which the wearing position initial probability as shown in the portion A of FIG. 10 is set from a storage unit (described later), an external storage medium connected thereto, or the like, as an example. Although the portion A of FIG. 10 illustrates an example in which the wearing probability in each wearing position is a fixed value, the wearing probability in each wearing position may be set by a probability distribution having deviation using a user's tendency or the like. An example of the probability distribution having deviation includes "increase in the probability of the wrist because the user typically wears the setting target device on the wrist" or the like.

The information processing apparatus according to the present embodiment determines whether a wearing position estimation termination condition is satisfied (S202). The information processing apparatus according to the present embodiment determines that the wearing position estimation termination condition is satisfied when the deviation of the wearing distribution is sufficiently large. More specifically, the information processing apparatus according to the present embodiment determines that the wearing position estimation termination condition is satisfied when the wearing probability at a wearing position becomes larger than or equal to a predetermined threshold, or when the wearing probability at a wearing position becomes larger than a predetermined threshold.

If it is determined in step S202 that the wearing position estimation termination condition is satisfied, the information processing apparatus according to the present embodiment terminates the wearing position recognition process related to the third example.

If it is not determined in step S202 that the wearing position estimation termination condition is satisfied, the information processing apparatus according to the present embodiment estimates the user's behavior on the basis of the detection value of the sensor corresponding to the setting target device (S204).

The information processing apparatus according to the present embodiment multiplies the probability distribution of the wearing position probability as shown in FIG. 10 by a value indicating likelihood of the behavior based on the detection value of the sensor corresponding to the setting target device, and estimates the behavior having a larger multiplication value as the user's behavior. In the probability distribution of the wearing position probability, the process for estimation of behavior is not necessary to be performed on the wearing position that is smaller than or equal to the preset probability or smaller than the preset probability.

Taking a specific example, when the user performs an activity, such as a case where the likelihood of a recognition device for recognizing soccer in the ankle is 50[%] or a case where the likelihood of a recognition device for recognizing a swing in the wrist is 60[%], the behavior as described below is estimated by the probability distribution of the wearing position probability.

In case where probability distribution of wearing position probability is the portion A of FIG. 10: the user's behavior is estimated as a swing by "60[%]×12.5>50[%]×12.5".

In case where probability distribution of wearing position probability is the portion B of FIG. 10: the user's behavior is estimated as soccer by "60[%]×20<50[%]×30".

The information processing apparatus according to the present embodiment estimates the wearing position on the basis of the estimation result of user's behavior as an example (S206). The information processing apparatus according to the present embodiment updates the wearing probability shown in FIG. 10 and estimates a wearing position having the largest wearing probability as the wearing position.

For example, in step S204, when the user's behavior is estimated as soccer and the likelihood is 80[%], the information processing apparatus according to the present embodiment increases the wearing probability of the ankle in the probability distribution of the wearing position probability shown in FIG. 10. The information processing apparatus according to the present embodiment may increase the wearing probability by a given quantity or may change a way to increase the wearing probability depending on the likelihood.

In addition, for example, in step S204, when the user's behavior is estimated as a "squat in the case where the sensor corresponding to the setting target device is worn on the neck", a "push-up in the case where the sensor corresponding to the setting target device is worn on the neck, and the likelihood of both cases is 30[%] or less, the information processing apparatus according to the present embodiment decreases the wearing probability of the neck. The information processing apparatus according to the present embodiment may decrease the wearing probability by a given quantity or may change a way to decrease the wearing probability depending on the likelihood (or a combination of likelihoods).

The information processing apparatus determines whether a wearing position probability reset condition is satisfied (S208). In this connection, the wearing position probability reset condition is a condition for resetting the wearing position probability when the wearing position is changed. For example, when a signal indicating that the setting target device is removed from the attachment is detected, the information processing apparatus according to the present embodiment determines that the wearing position probability reset condition is satisfied. In addition, for example, when the likelihood of a behavior recognition device corresponding to the wearing position with a low probability is to be significantly high, the information processing apparatus according to the present embodiment may determine that the wearing position probability reset condition is satisfied.

If it is determined in step S208 that the wearing position probability reset condition is satisfied, the information processing apparatus according to the present embodiment performs the process from step S200. On the other hand, if it is not determined in step S208 that the wearing position probability reset condition is satisfied, the information processing apparatus according to the present embodiment performs the process from step S202.

For example, by performing the wearing position recognition process according to the third example as shown in FIG. 9, the information processing apparatus according to the present embodiment can gradually narrow down the wearing position candidates by continuing the behavior with higher accuracy.

(4-4) Fourth Example of Wearing Position Recognition Process

The information processing apparatus according to the present embodiment recognizes the wearing position based on an operation signal based on the user operation for specifying the wearing position.

In this connection, examples of the operation signal include an operation signal conveyed from an operation unit (described later) included in the information processing apparatus according to the present embodiment and an operation signal that is transmitted from an external operation device such as a remote controller and is received by a communication unit (described later) or an external communication device connected thereto.

In addition, examples of the user operation for specifying the wearing position according to the present embodiment include any operation capable of specifying the wearing position such as an operation for specifying the wearing position by the user pressing a button or the like, a gesture operation in which the user performs a gesture indicating the wearing position, and an operation for specifying the wearing position by the user speaking the wearing position.

(4-5) Fifth Example of Wearing Position Recognition Process

The information processing apparatus according to the present embodiment recognizes the wearing position on the basis of the detection value of the sensor corresponding to the setting target device.

In this connection, the sensor corresponding to the setting target device according to the present embodiment, which is concerned with the fifth example of the wearing position recognition process, is a sensor included in the setting target device or an external sensor connected to the setting target device. Examples of the sensor according to the fifth example of the wearing position recognition process include a button, an illuminance sensor, a proximity sensor, an atmospheric pressure sensor. The sensor according to the fifth example of the wearing position recognition process may be included in the sensor used for behavior recognition corresponding to the setting target device, or may be a sensor separate from the sensor used for behavior recognition corresponding to the setting target device.

Figure 11:
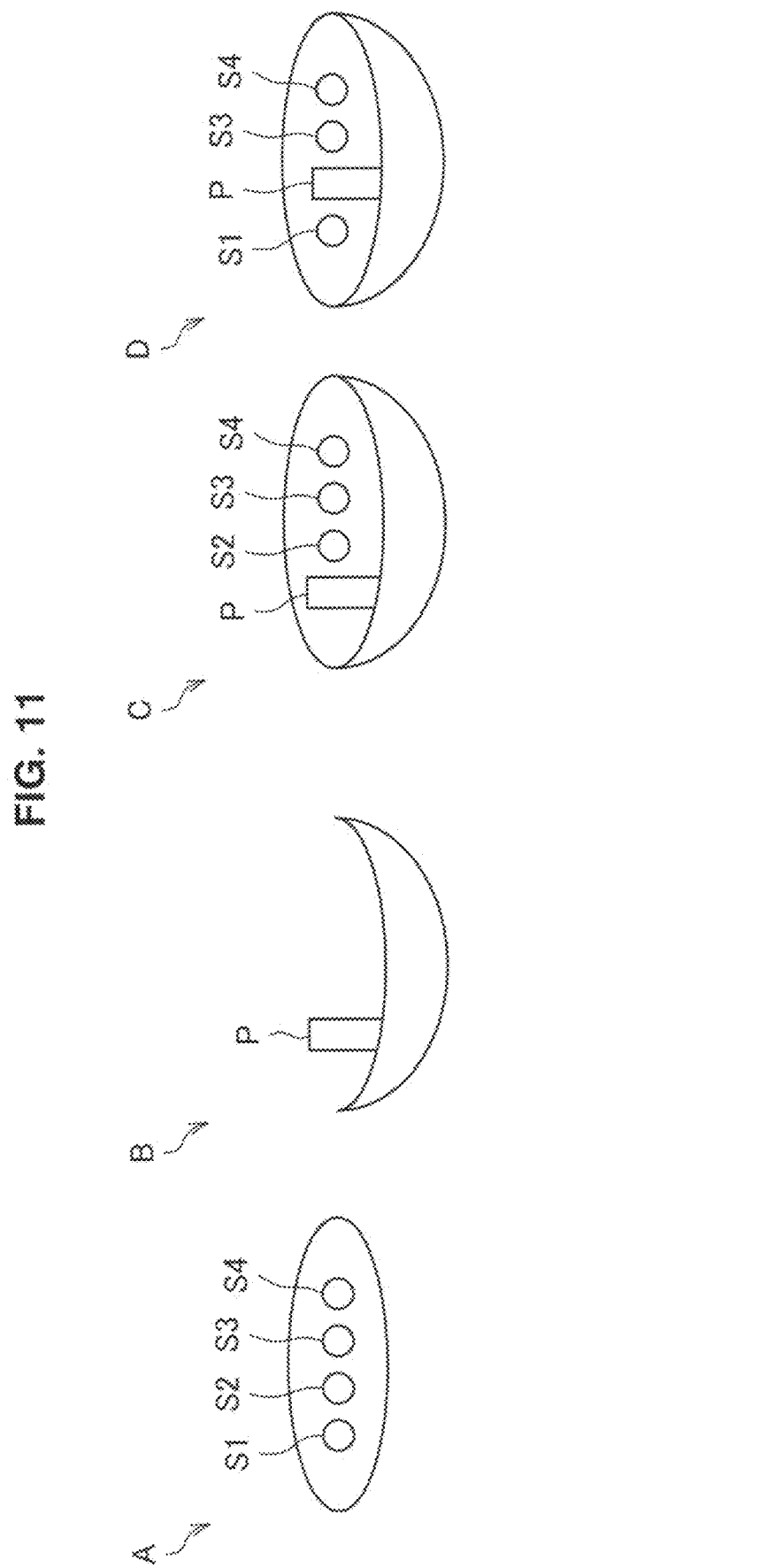
FIG. 11 is a diagram illustrated to describe a fifth example of a wearing position recognition process according to the present embodiment.

FIG. 11 is a diagram illustrated to describe the fifth example of the wearing position recognition process according to the present embodiment.

The portion A of FIG. 11 illustrates an example of a sensor unit corresponding to the setting target device, which is concerned with the fifth example of the wearing position recognition process. The parts S1 to S4 shown in the portion A of FIG. 11 illustrate an example of a sensor according to the fifth example of the wearing position recognition process. In addition, the portion B of FIG. 11 illustrates an attachment on which the sensor unit shown in the portion A of FIG. 11 can be worn. The part P in the portion B of FIG. 11 illustrates a protrusion that can be corresponded to each of the parts S1 to S4 shown in the portion A of FIG. 11.

In addition, the portions C and D of FIG. 11 illustrate an example of a case where the protrusion P corresponds to the sensor shown in the portion A of FIG. 11. The correspondence relation between the sensor shown in the portion A of FIG. 11 and the protrusion P shown in the portion B of FIG. 11 varies depending on the wearing position, as an example. In this connection, the correspondence of the sensor shown in the portion of FIG. 11 to the protrusion P shown in the portion B of FIG. 11 means that the protrusion P presses a button (an example of the sensor) or the protrusion P blocks an illuminance sensor, a proximity sensor, or an atmospheric pressure sensor (an example of the sensor).

For example, as shown in the portions C and D of FIG. 11, the correspondence of the sensor S1 or S2 to the protrusion P allows an electrical signal is transmitted in response to the depression of a button (an example of the sensor) or allows the detection value of the illuminance sensor, the proximity sensor, or the atmospheric pressure sensor (an example of the sensor) to be changed. The information processing apparatus according to the present embodiment recognizes the wearing position by the position of the button (an example of the sensor) to which the electrical signal is transmitted or the position in which the detection value of the illuminance sensor, the proximity sensor, or the atmospheric pressure sensor (an example of the sensor) is changed.

Although FIG. 11 illustrates an example in which the protrusion P is provided on the attachment side, there is possible to design a configuration in which a sensor (an example of the sensor corresponding to the setting target device) is provided on the attachment side and the protrusion P is provided on the setting target device side to be worn on the attachment.

(4-6) Sixth Example of Wearing Position Recognition Process

The information processing apparatus according to the present embodiment recognizes the wearing position on the basis of the detection value of the sensor corresponding to the setting target device and model data that is previously learned in each position at which the sensor can be worn.

The information processing apparatus according to the present embodiment recognizes the wearing position by pattern recognition or the like using the model data that is previously learned from the detection value of the sensor in each wearing position and the detection value of the sensor corresponding to the setting target device, as an example. In addition, the information processing apparatus according to the present embodiment can recognize the wearing position based on the detection value of the sensor by using the technique disclosed in JP 2006-340903A, which has been filed by the same applicant.

(Information Processing Apparatus According to Present Embodiment)

The following description will be given of an exemplary configuration of the information processing apparatus according to the present embodiment capable of performing the process of implementing the information processing method according to the present embodiment as described above.

Figure 12:
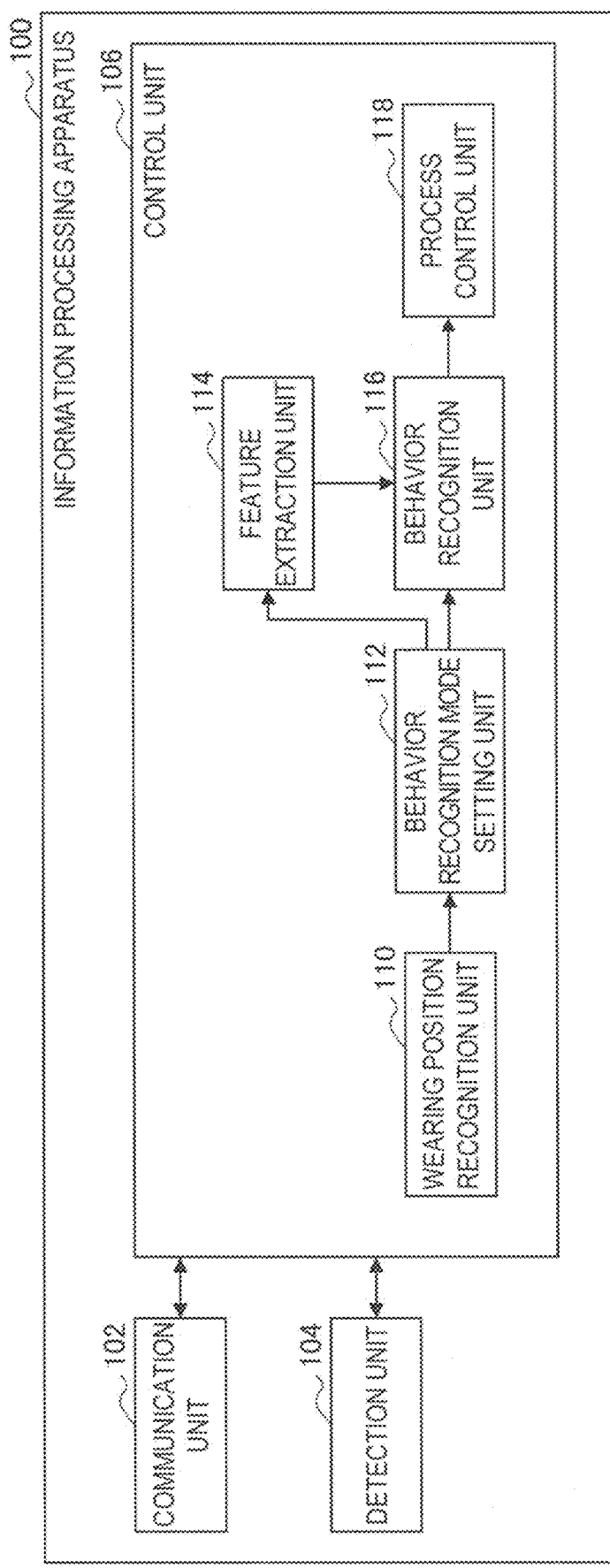
FIG. 12 is a block diagram illustrating an exemplary configuration of an information processing apparatus according to the present embodiment.

FIG. 12 is a block diagram illustrating an example of the configuration of the information processing apparatus 100 according to the present embodiment. The information processing apparatus 100 includes a communication unit 102, a detection unit 104, and a control unit 106, for example.

In addition, the information processing apparatus 100 may include read only memory (ROM) (not illustrated), random access memory (RAM) (not illustrated), a storage unit (not illustrated), an operation unit (not illustrated) operated by a user, and a display unit (not illustrated) for displaying various screens on a display screen, for example.

In the information processing apparatus 100, the structural elements are connected via a bus serving as a data transmission channel, for example.

The ROM (not illustrated) stores control data used by the control unit 106 such as programs and operation parameters. The RAM (not illustrated) stores temporarily programs or the like to be executed by the control unit 106.

The storage unit (not illustrated) is a storage means included in the information processing apparatus 100, and stores various data including the table shown in FIG. 8, data concerning the information processing method according to the present embodiment such as data indicating the probability distribution of the wearing position probability shown in FIG. 10, and applications. Examples of the storage unit (not illustrated) include a magnetic recording medium such as a hard disk, and nonvolatile memory such as flash memory. The storage unit (not illustrated) may be detachably attached to the information processing apparatus 100.

Examples of the operation unit (not illustrated) include an operation input device (to be described later). Examples of the display unit (not illustrated) include a display device (to be described later).

[Hardware Configuration Example of Information Processing Apparatus 100]

Figure 13:
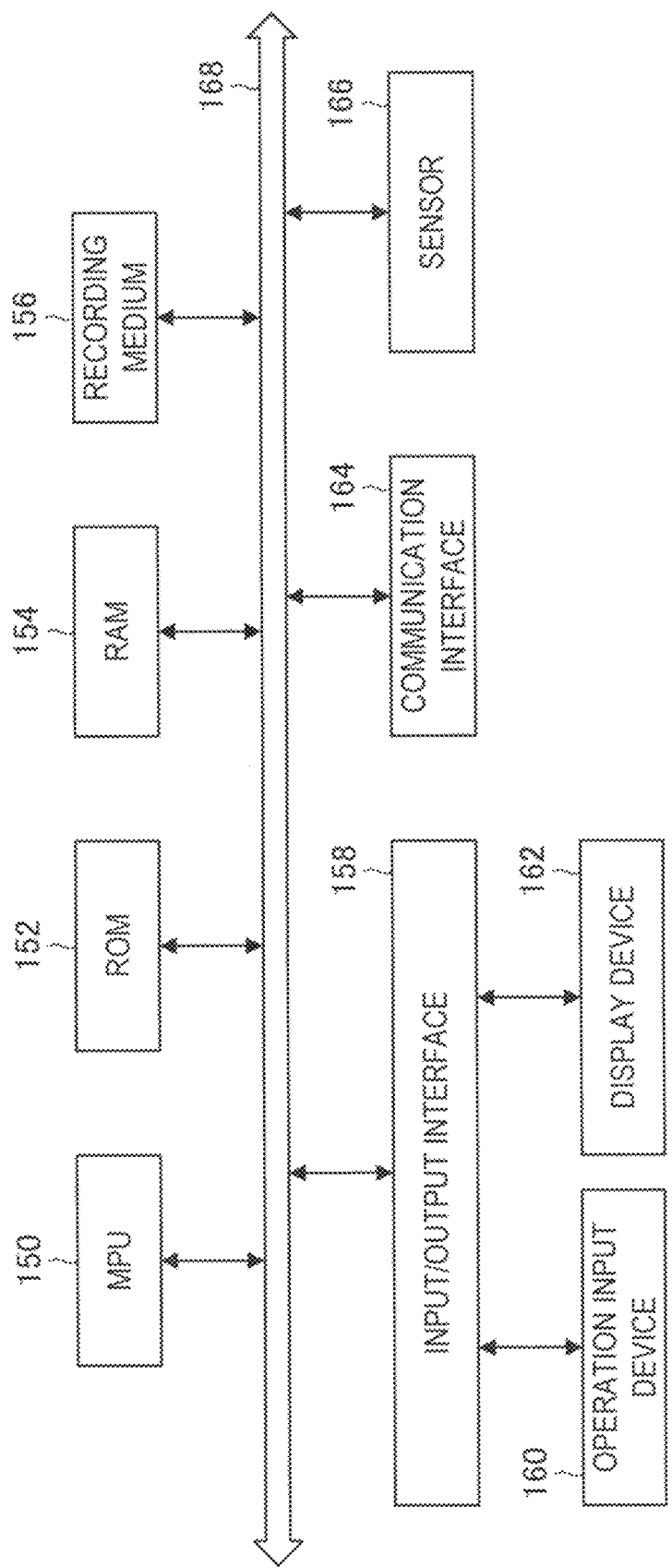
FIG. 13 is a diagram illustrating an example of a hardware configuration of the information processing apparatus according to the present embodiment.

FIG. 13 is an explanatory diagram illustrating an example of a hardware configuration of the information processing apparatus 100 according to the present embodiment. The information processing apparatus 100 includes an MPU 150, ROM 152, RAM 154, a recording medium 156, an input/output interface 158, an operation input device 160, a display device 162, a communication interface 164, and a sensor 166, for example. In the information processing apparatus 100, the structural elements are connected via a bus 168 serving as a data transmission channel, for example.

The MPU 150 is configured to include, for example, a processor composed of an arithmetic logic circuit or the like such as micro processing unit (MPU) and various processing circuits, and functions as the control unit 106 that controls the entire information processing apparatus 100. In addition, in the information processing apparatus 100, the MPU 150 serves as, for example, a wearing position recognition unit 110, a behavior recognition mode setting unit 112, a feature extraction unit 114, a behavior recognition unit 116, and a process control unit 118, which will be described later.

The ROM 152 stores control data such as operation parameters, programs, and the like used by the MPU 150. The RAM 154 temporarily stores programs and the like executed by the MPU 150, for example.

The recording medium 156 functions as the storage unit (not illustrated). For example, the recording medium 156 stores various kinds of data such as an application and data relating to the information processing method according to the present embodiment like the table shown in FIG. 8. Examples of the recording medium 156 include a magnetic recording medium such as a hard disk, and nonvolatile memory such as flash memory. The recording medium 156 may be detachably attached to the information processing apparatus 100.

The input/output interface 158 connects the operation input device 160 and the display device 162, for example. The operation input device 160 functions as the operation unit (not illustrated), and the display device 162 functions as the display unit (not illustrated). Examples of the input/output interface 158 include a universal serial bus (USB) terminal, a digital visual interface (DVI) terminal, a High-Definition Multimedia Interface (HDMI) (registered trademark) terminal, and various kinds of processing circuits.

The operation input device 160 is installed at the surface of the information processing apparatus 100, and connected to the input/output interface 158 in the information processing apparatus 100, for example. Examples of the operation input device 160 include a button, arrow keys, rotary type selectors such as jog dials, and a combination thereof.

The display device 162 is installed at the surface of the information processing apparatus 100, and connected to the input/output interface 158 in the information processing apparatus 100, for example. Examples of the display device 162 include a liquid crystal display, and an organic electroluminescence display (also referred to as an organic light emitting diode (OLED) display).

Of course, the input/output interface 158 is capable of being connected to an external device such as an external operation input device (for example, keyboard or mouse), an external display device, or an external sensor each of which serves as an external apparatus of the information processing apparatus 100. In addition, the display device 162 may be a device capable of displaying and being operated by a user such as a touchscreen.

The communication interface 164 is a communication mechanism included in the information processing apparatus 100, and functions as the communication unit 102 for communicating with an external apparatus such as an external setting target apparatus in a wired/wireless manner via a network (or directly). Here, examples of the communication interface 164 include IEEE 802.11 port and transmission/reception circuit (wireless communication), IEEE 802.15.1 port and transmission/reception circuit (wireless communication), communication antenna and RF circuit (wireless communication), local area network (LAN) terminal and transmission/reception circuit (wired communication), and the like. In addition, examples of the network according to the present embodiment may include a wired network such as LAN or WAN (Wide Area Network), a wireless network such as wireless WAN (WWAN; Wireless Wide Area Network) via a base station or wireless LAN (WMAN; Wireless Local Area Network), Internet using a communication protocol such as TCP/IP (Transmission Control Protocol/Internet Protocol), and the like.

The sensor 166 is a sensor to be used for behavior recognition included in the information processing apparatus 100, and functions as the detection unit 104. Examples of the sensor 166 include any sensors to be used for the process for behavior recognition of a user, such as an acceleration sensor, a GPS device, a gyro sensor, an atmospheric pressure sensor, a proximity sensor, or a biosensor. The sensor 166 may be a sensor group including a plurality of sensors.

The sensor 166 may be intended for serving as a sensor (the sensor according to the fifth example of the wearing position recognition process) for implementing the process of the above item (4) (wearing position recognition process) described above.

The information processing apparatus 100 carries out the process relating to the information processing method according to the present embodiment by the configuration illustrated in FIG. 13, for example. Note that, the hardware configuration of the information processing apparatus 100 according to the present embodiment is not limited to the configuration in FIG. 13.

For example, when the setting target device is an external device, the information processing apparatus 100 may have a configuration that does not include the sensor 166. In the case where the information processing apparatus 100 is the setting target device, when an external device having a similar function to the sensor 166 is connected to the information processing apparatus 100, the information processing apparatus 100 may have a configuration that does not include the sensor 166.

In addition, for example, in the case where the information processing apparatus 100 communicates with the external apparatus via a connected external communication device, the information processing apparatus 100 does not have to include the communication interface 164. In addition, the information processing apparatus 100 may be configured not to include the recording medium 156, the operation device 160, or the display device 162.

With reference to FIG. 12 again, the example of the configuration of the information processing apparatus 100 will be described. The communication unit 102 is a communication mechanism included in the information processing apparatus 100, and communicates with an external apparatus such as an external setting target apparatus in a wired/wireless manner via a network (or directly). The communication performed by the communication unit 102 is controlled by the control unit 106, for example.

Examples of the communication unit 102 include a communication antenna, an RF circuit, a LAN terminal, and a transmission/reception circuit. However, the communication unit 102 is not limited thereto. For example, the communication unit 102 may have a configuration corresponding to any standard that enables communication such as a USB terminal or the transmission/reception circuit, or any configuration capable of communicating with the external apparatus via the network.

The detection unit 104 has the sensor used for behavior recognition included in the information processing apparatus 100 and outputs the detection value. Examples of the detection unit 104 include any sensors to be used for the process for behavior recognition of a user, such as an acceleration sensor or a GPS device. The detection unit 104 may be constituted of a sensor group including a plurality of sensors. The sensor provided in the detection unit 104 may be intended for serving as a sensor (the sensor according to the fifth example of the wearing position recognition process) for implementing the process of the above item (4) (wearing position recognition process) described above.

The control unit 106 is configured to include, for example, an MPU, and is intended for controlling the entire information processing apparatus 100. The control unit 106 is configured to include a wearing position recognition unit 110, a behavior recognition mode setting unit 112, a feature extraction unit 114, a behavior recognition unit 116, and a process control unit 118. The control unit 106 plays a leading role in performing the process of implementing the information processing method according to the present embodiment.

The control unit 106 may further include a communication control unit (not illustrated) for controlling communication in the communication unit 102, for example. The communication control unit (not illustrated) controls exchange of various kinds of information. The function of the communication control unit (not illustrated) may be carried out by another structural element such as the communication unit 102.

The wearing position recognition unit 110 plays a leading role in performing the process of the above item (4) (wearing position recognition process) and recognizes the wearing position. The wearing position recognition unit 110 recognizes the wearing position by performing any process of the wearing position recognition process according to the first example described in the above item (4-1) to the wearing position recognition process according to the sixth example described in the above item (4-6). When the wearing position recognition unit 110 performs the wearing position recognition process according to the third example described in the above item (4-3), the information processing apparatus according to the present embodiment plays a role in performing the process in step S204 of FIG. 10, and may further include a wearing position estimation unit (not shown) configured to estimate the wearing position.

The behavior recognition mode setting unit 112 plays a leading role in performing the process of the above item (1) (behavior recognition mode setting process), and sets the behavior recognition mode on the basis of the wearing position information of the setting target device. The behavior recognition mode setting unit 112 sets the behavior recognition mode by performing a process for setting the behavior recognition mode according to the first example described in the above item (1-1) or a process for setting the behavior recognition mode according to the second example described in the above item (1-2).

The feature extraction unit 114 extracts a feature amount of the type used for behavior recognition corresponding to the set behavior recognition mode from the detection results of the detection unit 104, as an example. The information processing apparatus according to the present embodiment may have a configuration that does not include the feature extraction unit 114.

The behavior recognition unit 116 plays a leading role in performing the process of the above item (2) (behavior recognition process), and recognizes the user's behavior on the basis of the set behavior recognition mode and the detection value of the sensor corresponding to the setting target device, such as detection value of the detection unit 104. The behavior recognition unit 116 recognizes a predetermined behavior on the basis of an algorithm or model data corresponding to the set behavior recognition mode and the feature amount extracted by the feature extraction unit 114, as an example. When the configuration is implemented without the feature extraction unit 114, the behavior recognition unit 116 recognizes a predetermined behavior on the basis of an algorithm or model data corresponding to the set behavior recognition mode and the detection value of the sensor corresponding to the setting target device.

The process control unit 118 plays a leading role in performing the process of the above item (3) (execution control process), and controls the execution of the process corresponding to the user's behavior recognized by the behavior recognition unit 116. The process control unit 118 is also possible to control the execution of the process corresponding to the wearing position indicated by the wearing position information and the user's behavior recognized by the behavior recognition unit 116. The process control unit 118 performs the process of the first example described in the above item (a) to the process of the eighth example described in the above item (h).

The control unit 106 plays a leading role in performing the process of implementing the information processing method according to the present embodiment by including the wearing position recognition unit 110, the behavior recognition mode setting unit 112, the feature extraction unit 114, the behavior recognition unit 116, and the process control unit 118, as an example.

The information processing apparatus 100 having the configuration, for example, illustrated in FIG. 12 allows the process of implementing the information processing method according to the present embodiment (e.g., the process of the above item (1) (behavior recognition mode setting process) to the process of the above item (4) (wearing position recognition process)) to be performed.

Thus, the information processing apparatus 100 having the configuration illustrated in FIG. 12 for example allows the user's behavior to be recognized with higher accuracy and allows the process depending on the recognized user's behavior to be controlled.

In addition, by the configuration illustrated in FIG. 12, the information processing apparatus 100 has effects such as the above described effect achieved by carrying out the process relating to the information processing method according to the present embodiment, for example.

Note that, the configuration of the information processing apparatus according to the present embodiment is not limited to the configuration in FIG. 12.

For example, when the wearing information indicating the wearing position recognized by an external device having a similar function to the wearing position recognition unit 110 illustrated in FIG. 12 is acquired through the communication unit 102 or the like, the information processing apparatus according to the present embodiment may have a configuration that does not include the wearing position recognition unit 110. Even when the configuration is implemented without the wearing position recognition unit 110, the information processing apparatus according to the present embodiment is possible to perform the process of the above item (1) (behavior recognition mode setting process) to the process of the above item (3) (execution control process). Thus, even when the configuration is implemented without the wearing position recognition unit 11, the information processing apparatus according to the present embodiment is possible to recognize the user's behavior with higher accuracy and to control the process depending on the recognized user's behavior.

The information processing apparatus according to the present embodiment can be configured to include one or more of the wearing position recognition unit 110, the behavior recognition mode setting unit 112, the feature extraction unit 114, the behavior recognition unit 116, and the process control unit 118 illustrated in FIG. 12 as a separate component (e.g., implemented as a separate processing circuit) from the control unit 106.

For example, when the setting target device is an external device, the information processing apparatus according to the present embodiment may have a configuration that does not include the detection unit 104. In the case where the information processing apparatus 100 is the setting target device, when an external device having a similar function to the detection unit 104 is connected to the information processing apparatus 100, the information processing apparatus according to the present embodiment may have a configuration that does not include the detection unit 104.

In the case where communication with the external apparatus is established via an external communication device having a function and configuration similar to the communication unit 102, the information processing apparatus according to the present embodiment does not have to include the communication unit 102, for example.

The information processing apparatus has been described as present embodiment. However, the present embodiment is not limited thereto. The present embodiment is applied to various kinds of portable equipment such as a communication apparatus like a mobile phone or a smartphone, a tablet apparatus, a video/music reproduction apparatus (or video/music recording and reproduction apparatus), a game console, and a computer such as a laptop personal computer (PC). The present embodiment may also be applied to a wearable apparatus, for example. The present embodiment may also be applied to the various equipment difficult to carry such as a server or a computer like a desktop PC. In addition, the present embodiment may also be applied to a processing integrated circuit (IC) which can be installed in the above-described equipment.

For example, when the setting target device is an external device, it is possible to implement an information processing system including the information processing device and one or more setting target devices as a cloud computing information processing system.

(Program According to the Present Embodiment)
[i] Program for Implementing Information Processing Apparatus A program for causing a computer to function as the information processing apparatus according to the present embodiment (e.g., program capable of executing the process of implementing the information processing method according to the present embodiment, such as the process of the above item (1) (behavior recognition mode setting process) to the process of the above item (3) (execution control process) or the process of the above item (1) (behavior recognition mode setting process) to the process of the above item (4) (wearing position recognition process)) is executed by a processor or like device in the computer, and thus it is possible to recognize the user's behavior with higher accuracy and to control the process depending on the recognized user's behavior. Furthermore, it is possible to achieve advantageous effects obtained by performing the process of implementing the information processing method according to the present embodiment described above by allowing a program for causing a computer to function as the information processing apparatus according to the present embodiment to be executed by a processor or the like in the computer.

The preferred embodiments of the present disclosure have been described above with reference to the accompanying drawings, whilst the present invention is not limited to the above examples, of course. A person skilled in the art may find various alternations and modifications within the scope of the appended claims, and it should be understood that they will naturally come under the technical scope of the present disclosure.

For example, it has been illustrated above that a program (computer program) that causes a computer to function as the information processing apparatus according to the present embodiment is provided, but the present embodiment can further provide a recording medium in which the above-described program is stored together.

The above configuration shows an example of the present embodiment and naturally comes under the technical scope of the present disclosure.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1) An information processing apparatus including:
a behavior recognition mode setting unit configured to set a behavior recognition mode on a basis of wearing position information of a setting target device;
a behavior recognition unit configured to recognize user's behavior on a basis of the set behavior recognition mode and a detection value of a sensor corresponding to the setting target device; and
a process control unit configured to control execution of a process corresponding to the recognized user's behavior.

(2) The information processing apparatus according to (1),
wherein the behavior recognition mode includes a sensor-related setting, and
wherein the behavior recognition mode setting unit performs the sensor-related setting based on the wearing position information on the sensor corresponding to the setting target device to set the behavior recognition mode.

(3) The information processing apparatus according to (2),
wherein the sensor-related setting includes one or both of a setting of a type of a sensor and a setting of a parameter of the sensor.

(4) The information processing apparatus according to any one of (1) to (3),
wherein the behavior recognition mode includes a setting relating to a process for behavior recognition, and
wherein the behavior recognition mode setting unit performs the setting relating to the process for behavior recognition based on the wearing position information to set the behavior recognition mode.

(5) The information processing apparatus according to (4),
wherein the setting relating to the process for behavior recognition includes one or more of a setting of a type of a feature amount used for behavior recognition among detection values of the sensor corresponding to the setting target device, a setting of an algorithm used in the process for behavior recognition, and a setting of model data used in the process for behavior recognition.

(6) The information processing apparatus according to any one of (1) to (5), further including:
a wearing position recognition unit configured to recognize a wearing position at which the setting target device is worn by a user,
wherein the behavior recognition mode setting unit sets the behavior recognition mode on a basis of the wearing position information indicating the wearing position recognized in the wearing position recognition unit, and
wherein the process control unit controls execution of the process on a basis of the wearing position information indicating the wearing position recognized in the wearing position recognition unit.

(7) The information processing apparatus according to (6),
wherein the wearing position recognition unit recognizes the wearing position on a basis of a detection value of a sensor corresponding to the setting target device and a condition corresponding to a possible position on which the sensor is worn.

(8) The information processing apparatus according to (6),
wherein the wearing position recognition unit recognizes the wearing position on a basis of a detection value of a sensor corresponding to the setting target device and an output of a reference device as a reference to recognize the wearing position.

(9) The information processing apparatus according to (6),
wherein the wearing position recognition unit
estimates the wearing position on a basis of a result obtained by estimating user's behavior on a basis of a detection value of a sensor corresponding to the setting target device, and
recognizes the wearing position obtained by the estimation as the wearing position.

(10) The information processing apparatus according to (6),
wherein the wearing position recognition unit recognizes the wearing position on a basis of an operation signal based on a user operation for specifying the wearing position.

(11) The information processing apparatus according to (6),
wherein the wearing position recognition unit recognizes the wearing position on a basis of a detection value of a sensor corresponding to the setting target device.

(12) The information processing apparatus according to (6),
wherein the wearing position recognition unit recognizes the wearing position on a basis of a detection value of a sensor corresponding to the setting target device and model data previously learned at each possible position on which the sensor is worn.

(13) The information processing apparatus according to any one of (1) to (12), further including:
a detection unit configured to include a sensor corresponding to the setting target device,
wherein the behavior recognition unit recognizes user's behavior on a basis of a detection value of the detection unit.

(14) An information processing method executed by an information processing apparatus, the information processing method including:
a step of setting a behavior recognition mode on a basis of wearing position information of a setting target device;
a step of recognizing user's behavior on a basis of the set behavior recognition mode and a detection value of a sensor corresponding to the setting target device; and
a step of controlling execution of a process corresponding to the recognized user's behavior.

(15) A program for causing a computer to execute:
a step of setting a behavior recognition mode on a basis of wearing position information of a setting target device;
a step of recognizing user's behavior on a basis of the set behavior recognition mode and a detection value of a sensor corresponding to the setting target device; and
a step of controlling execution of a process corresponding to the recognized user's behavior.

REFERENCE SIGNS LIST 100 information processing apparatus
102 communication unit
104 detection unit
106 control unit
110 wearing position recognition unit
112 behavior recognition mode setting unit
114 feature extraction unit
116 behavior recognition unit
118 process control unit

The invention claimed is:

1. An information processing apparatus, comprising:
a behavior recognition mode setting unit configured to set a behavior recognition mode based on wearing position information of a setting target device, wherein the wearing position information of the setting target device indicates a wearing position of the setting target device on a user;
a behavior recognition unit configured to recognize a behavior of the user based on the set behavior recognition mode and a detection value of a sensor, wherein the sensor corresponds to the setting target device; and
a process control unit configured to control an application corresponding to the wearing position information and the recognized behavior.

2. The information processing apparatus according to claim 1, wherein
the behavior recognition mode includes a sensor-related setting;
the behavior recognition mode setting unit is further configured to:
apply the sensor-related setting on the sensor based on the wearing position information; and
set the behavior recognition mode based on the application of the sensor-related setting.

3. The information processing apparatus according to claim 2, wherein the sensor-related setting includes at least one of a first setting of a type of the sensor or a second setting of a parameter of the sensor.

4. The information processing apparatus according to claim 1, wherein
the behavior recognition mode includes a specific setting associated with a process for the recognition of the behavior, and
the behavior recognition mode setting unit is further configured to:
apply the specific setting based on the wearing position information; and
set the behavior recognition mode based on the application of the specific setting.

5. The information processing apparatus according to claim 4, wherein the specific setting includes at least one of a first setting of a type of a feature amount for the recognition of the behavior, a second setting of an algorithm associated with the process for the recognition of the behavior, or a third setting of model data associated with the process for the recognition of the behavior.

6. The information processing apparatus according to claim 1, further comprising
a wearing position recognition unit configured to recognize the wearing position of the setting target device.

7. The information processing apparatus according to claim 6, wherein the wearing position recognition unit is further configured to recognize the wearing position based on the detection value of the sensor and a condition corresponding to a possible position of the sensor.

8. The information processing apparatus according to claim 6, wherein the wearing position recognition unit is further configured to recognize the wearing position based on the detection value of the sensor and an output of a reference device.

9. The information processing apparatus according to claim 6, wherein the wearing position recognition unit is further configured to estimate the wearing position based on the recognized behavior of the user.

10. The information processing apparatus according to claim 6, wherein
the wearing position recognition unit is further configured to recognize the wearing position based on an operation signal, and
the operation signal is based on a user operation for the wearing position.

11. The information processing apparatus according to claim 6, wherein the wearing position recognition unit is further configured to recognize the wearing position based on the detection value of the sensor.

12. The information processing apparatus according to claim 6, wherein the wearing position recognition unit is further configured to recognize the wearing position based on the detection value of the sensor and model data, and the model data corresponds to each position on the user on which the sensor is wearable.

13. The information processing apparatus according to claim 1, further comprising a detection unit including the sensor.

14. An information processing method comprising:

setting a behavior recognition mode based on wearing position information of a setting target device, wherein the wearing position information of the setting target device indicates a wearing position of the setting target device on a user;

recognizing a behavior of the user based on the set behavior recognition mode and a detection value of a sensor, wherein the sensor corresponds to the setting target device; and controlling an application corresponding to the wearing position information and the recognized behavior.

15. A non-transitory computer-readable medium having stored thereon, computer-executable instructions which, when executed by a computer, cause the computer to execute operations, the operations comprising:

setting a behavior recognition mode based on wearing position information of a setting target device, wherein the wearing position information of the setting target device indicates a wearing position of the setting target device on a user;

recognizing a behavior of the user based on the set behavior recognition mode and a detection value of a sensor, wherein the sensor corresponds to the setting target device; and controlling an application corresponding to the wearing position information and the recognized behavior.

* * * * *